(12) United States Patent
Justino

(10) Patent No.: US 7,261,732 B2
(45) Date of Patent: Aug. 28, 2007

(54) STENT MOUNTED VALVE

(76) Inventor: Henri Justino, 7171 Buffalo Speedway, Unit # 1435, Houston, TX (US) 77025

( * ) Notice: Subject to any disclaimer, the term of this patent is extended or adjusted under 35 U.S.C. 154(b) by 487 days.

(21) Appl. No.: 10/741,427

(22) Filed: Dec. 22, 2003

(65) Prior Publication Data

US 2005/0137682 A1 Jun. 23, 2005

(51) Int. Cl.
*A61F 2/06* (2006.01)
*A61F 2/24* (2006.01)

(52) U.S. Cl. .................. 623/1.24; 623/1.26; 623/2.15; 623/2.19

(58) Field of Classification Search ............... 623/1.24, 623/1.26, 2.12, 2.13, 2.14, 2.15, 2.16, 2.17, 623/2.18, 2.19
See application file for complete search history.

(56) References Cited

U.S. PATENT DOCUMENTS

| | | | |
|---|---|---|---|
| 4,265,694 A * | 5/1981 | Boretos et al. ............. | 156/242 |
| 4,470,157 A * | 9/1984 | Love ......................... | 623/2.15 |
| 4,510,628 A * | 4/1985 | Kolff ......................... | 623/2.19 |
| 4,692,164 A * | 9/1987 | Dzemeshkevich et al. . | 623/2.14 |
| 5,397,351 A | 3/1995 | Pavcnik | |
| 5,545,215 A * | 8/1996 | Duran ........................ | 623/1.26 |
| 5,855,597 A | 1/1999 | Jayaraman | |
| 5,855,601 A | 1/1999 | Bessler et al. | |
| 5,855,610 A * | 1/1999 | Vacanti et al. ............ | 623/2.13 |
| 5,925,063 A | 7/1999 | Khosravi | |
| 5,957,949 A | 9/1999 | Leonhardt | |
| 6,287,334 B1 | 9/2001 | Moll | |
| 6,425,916 B1 | 7/2002 | Garrison | |
| 6,440,164 B1 | 8/2002 | DiMatteo | |
| 6,482,228 B1 | 11/2002 | Norred | |
| 6,503,272 B2 | 1/2003 | Duerig | |
| 6,517,576 B2 * | 2/2003 | Gabbay ...................... | 623/2.14 |
| 6,569,196 B1 | 5/2003 | Vesely | |

(Continued)

FOREIGN PATENT DOCUMENTS

EP 1 057 460 A1 12/2000

(Continued)

OTHER PUBLICATIONS

Transcatheter Implantation of a Bovine Valve in Pulmonary Position, Philipp Bonhoeffer et al. Service de Cardiologie Pédiatrique, Hôpital Necker Enfants Malades, Paris, France, Mar. 16, 2000, pp. 813-816.

(Continued)

*Primary Examiner*—Corrine McDermott
*Assistant Examiner*—Thomas J Sweet

(57) ABSTRACT

There is described a prosthetic valve to be inserted into a body lumen, the valve having leaflets that are spread apart during forward flow of fluid to create an orifice, and the leaflets coming into contact with each other during reverse flow of fluid, thereby impeding the reverse flow of fluid, the valve comprising: a hollow, cylindrical stent having an inner surface and an outer surface, and having a first and a second open end; and valve means formed from a single tubular membrane, the membrane mounted to the stent, the membrane having a graft portion internally folded and bonded to itself at a plurality of points to form pouches such that the leaflets extend from the pouches, and a sleeve portion on an outer surface of the stent to secure the membrane thereto.

14 Claims, 18 Drawing Sheets

U.S. PATENT DOCUMENTS

| | | | |
|---|---|---|---|
| 6,582,462 B1 | 6/2003 | Andreson | |
| 6,755,856 B2* | 6/2004 | Fierens et al. | 623/1.15 |
| 7,018,404 B2* | 3/2006 | Holmberg et al. | 623/1.26 |
| 2001/0021872 A1* | 9/2001 | Bailey et al. | 623/1.24 |
| 2002/0045936 A1* | 4/2002 | Moe | 623/2.17 |
| 2002/0090725 A1* | 7/2002 | Simpson et al. | 435/402 |
| 2002/0198594 A1 | 12/2002 | Schreck | |
| 2003/0023300 A1 | 1/2003 | Bailey et al. | |
| 2003/0028224 A1* | 2/2003 | McVenes et al. | 607/36 |
| 2003/0109924 A1 | 6/2003 | Cribier | |
| 2003/0130729 A1 | 7/2003 | Paniagua et al. | |
| 2003/0171802 A1* | 9/2003 | Wilder et al. | 623/1.24 |
| 2003/0204243 A1* | 10/2003 | Shiu | 623/1.16 |
| 2004/0037813 A1* | 2/2004 | Simpson et al. | 424/93.7 |
| 2004/0225352 A1* | 11/2004 | Osborne et al. | 623/1.24 |
| 2005/0027348 A1* | 2/2005 | Case et al. | 623/1.24 |
| 2005/0096736 A1* | 5/2005 | Osse et al. | 623/1.26 |
| 2005/0113910 A1* | 5/2005 | Paniagua et al. | 623/2.14 |
| 2005/0137681 A1* | 6/2005 | Shoemaker et al. | 623/1.23 |
| 2005/0137682 A1* | 6/2005 | Justino | 623/1.24 |
| 2005/0240262 A1* | 10/2005 | White | 623/2.12 |
| 2006/0136044 A1* | 6/2006 | Osborne et al. | 623/1.24 |

FOREIGN PATENT DOCUMENTS

| | | |
|---|---|---|
| EP | 1 251 805 | 11/2001 |
| WO | WO93/15693 | 7/1993 |
| WO | WO 00/47136 | 8/2000 |
| WO | WO 00/48531 | 8/2000 |
| WO | WO 02/47575 | 6/2002 |
| WO | WO 03/047468 | 6/2003 |
| WO | WO 03/092554 A1 | 11/2003 |

OTHER PUBLICATIONS

Steps Toward Percutaneous Aortic Valve Replacement, Younes Boudjemline et al. Service de Cardiologie Pédiatrique, Hôpital Necker Enfants Malades, Paris, France, Nov. 26, 2001, pp. 775-778.

Chronic Venous Insufficiency and Bioprosthetic Bicuspid Square Stent Based Venous Valve for Transcatheter Placement, Dusan Pavcnik, Dotter Interventional Institute, Oregon Health Sciences University, Portland, Oregon, 3$^{rd}$ Congress of Croatian Society of Radiology with International Participation, Acta clin Croat 2002; 41 (Suppl): pp. 93-97.

Off-bypass Implantation of a Self-expandable Valved Stent between Inferior Vena Cava and Right Atrium, Antonio F. Corno et al., Dept. of Cardiovascular Surgery, Centre Hospitalier Universitaire Vaudois, Lausanne, Switzerland, Sep. 12, 2001, pp. 1-4.

Percutaneous Transcatheter Implantation of an Aortic Valve Prosthesis for Calcific Aortic Stenosis, Alain Cribier et al., Dept. of Cardiology, Charles Nicolle Hospital, University of Rouen, FRANCE, Dec. 10, 2002, pp. 3006-3008.

Percutaneous Valve Implantation: Past, Present and Futur, Younes Boudjemline et al., Vol. 3, No. 2, Aug. 2002, pp. 1-11.

* cited by examiner

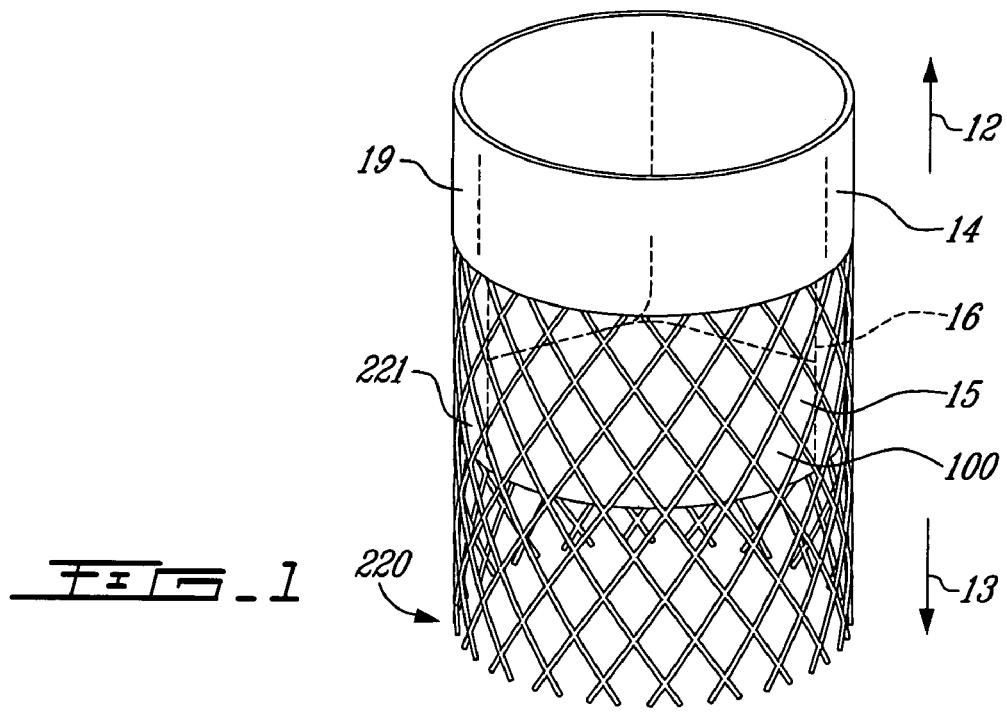
FIG_1
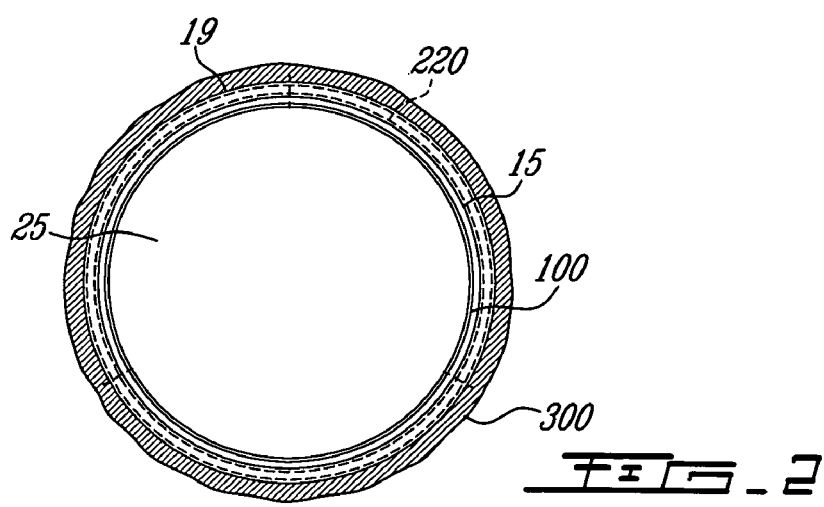
FIG_2
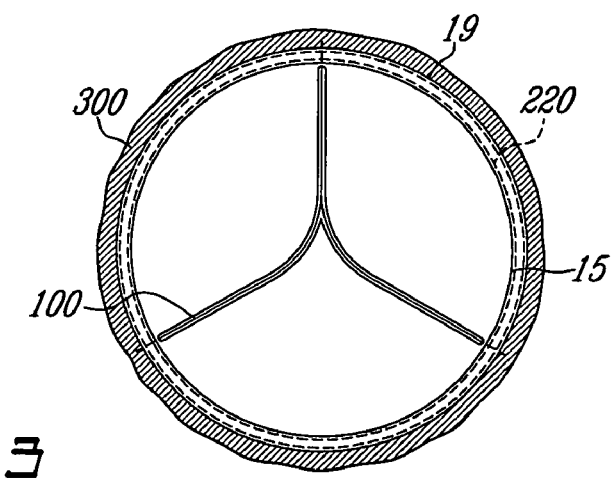
FIG_3

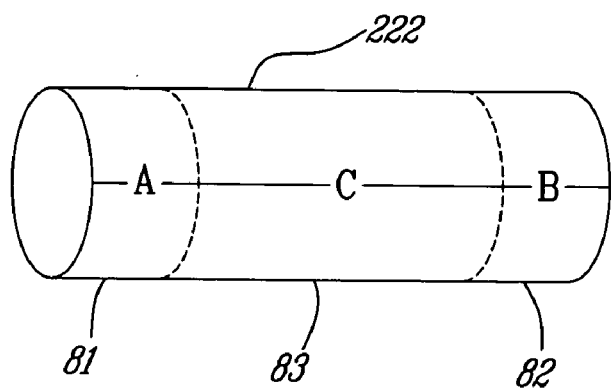
FIG_8A
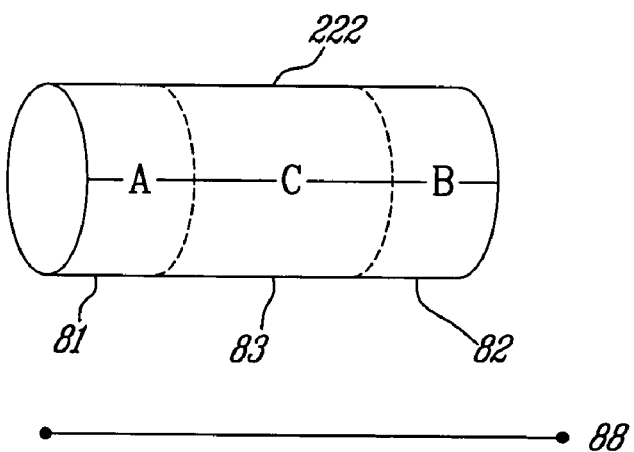
FIG_8B
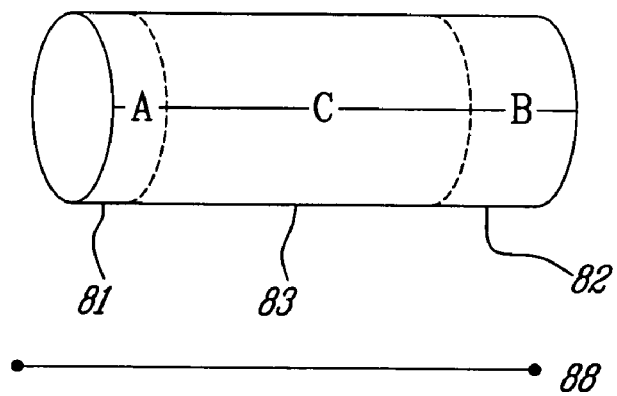
FIG_8C

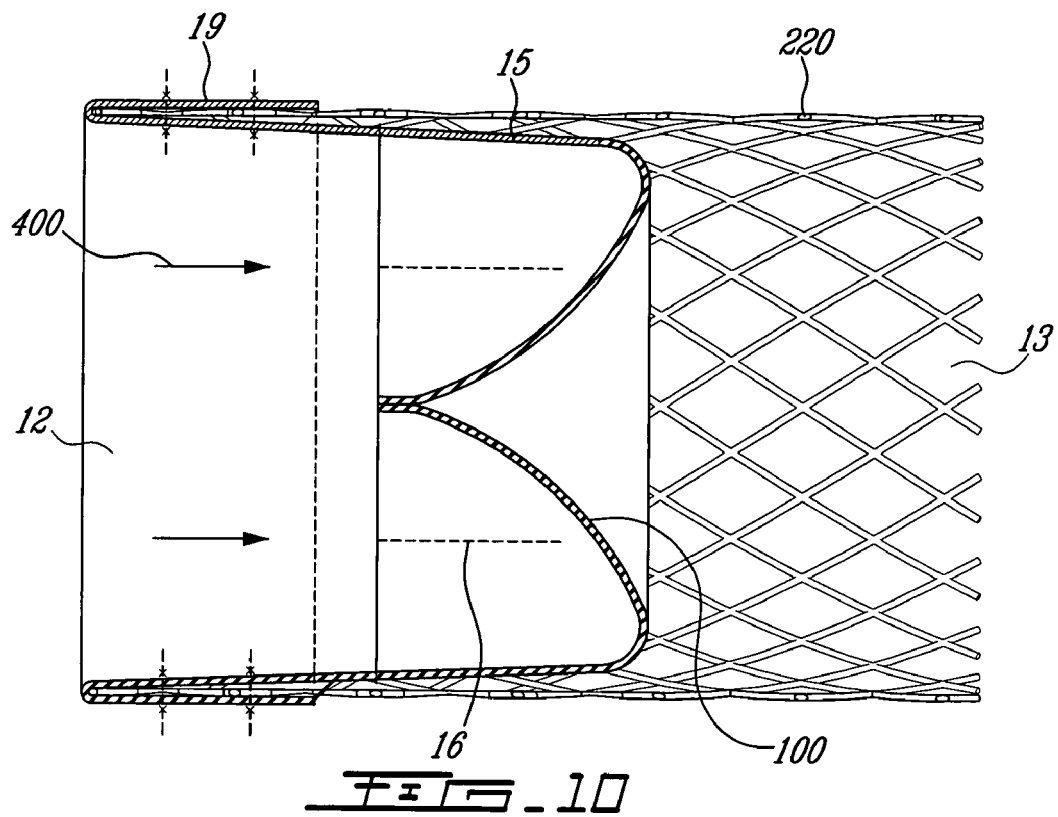
FIG_10
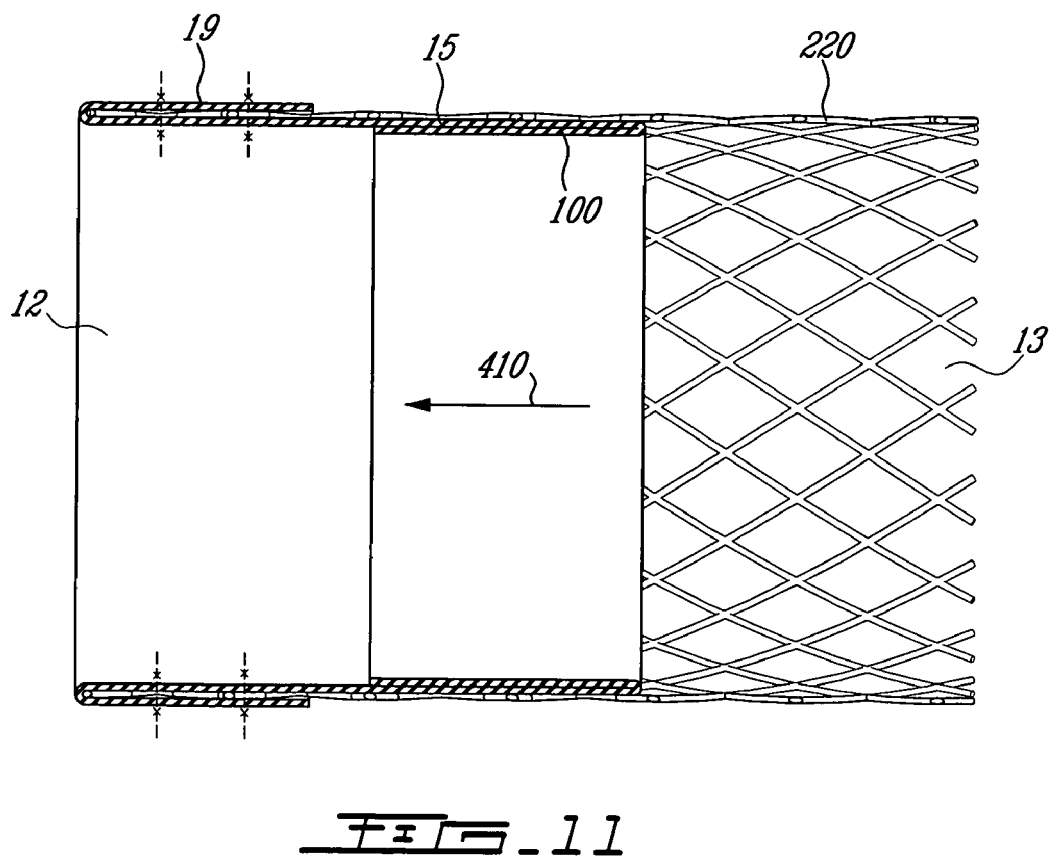
FIG_11

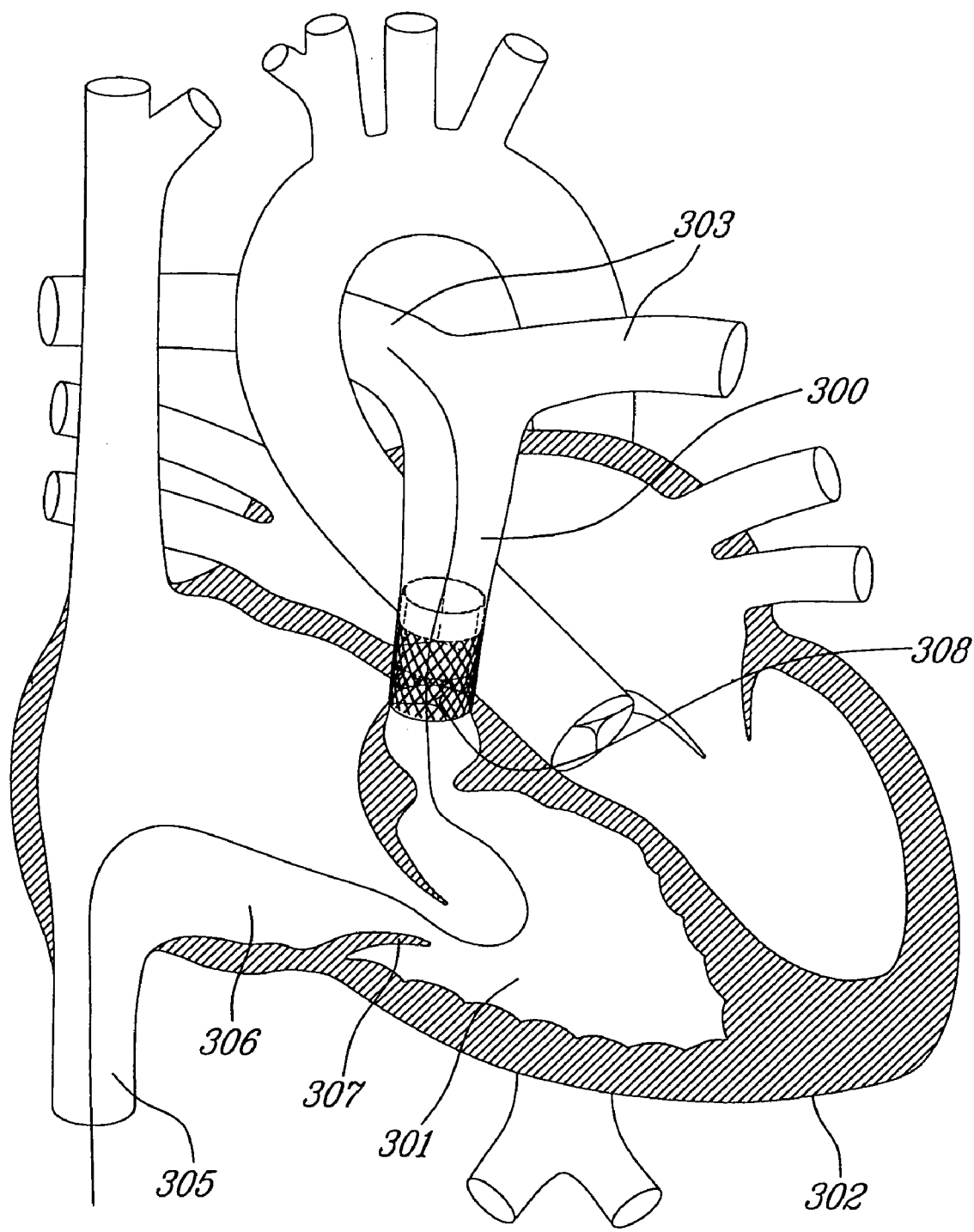
FIG_19

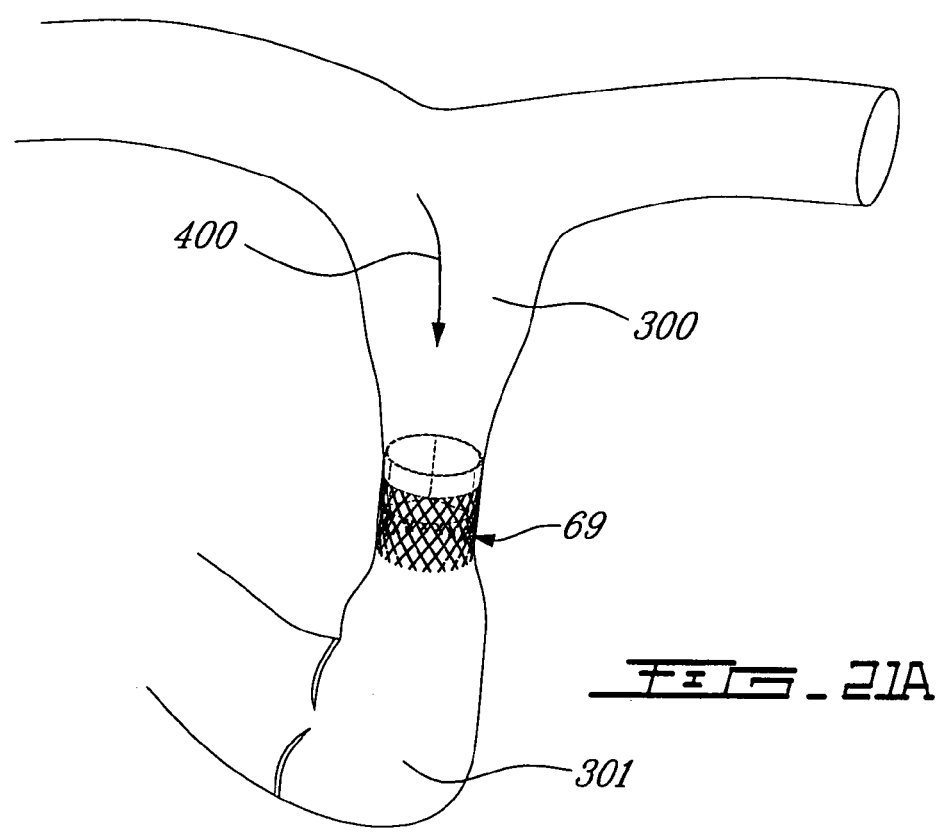
FIG_21A
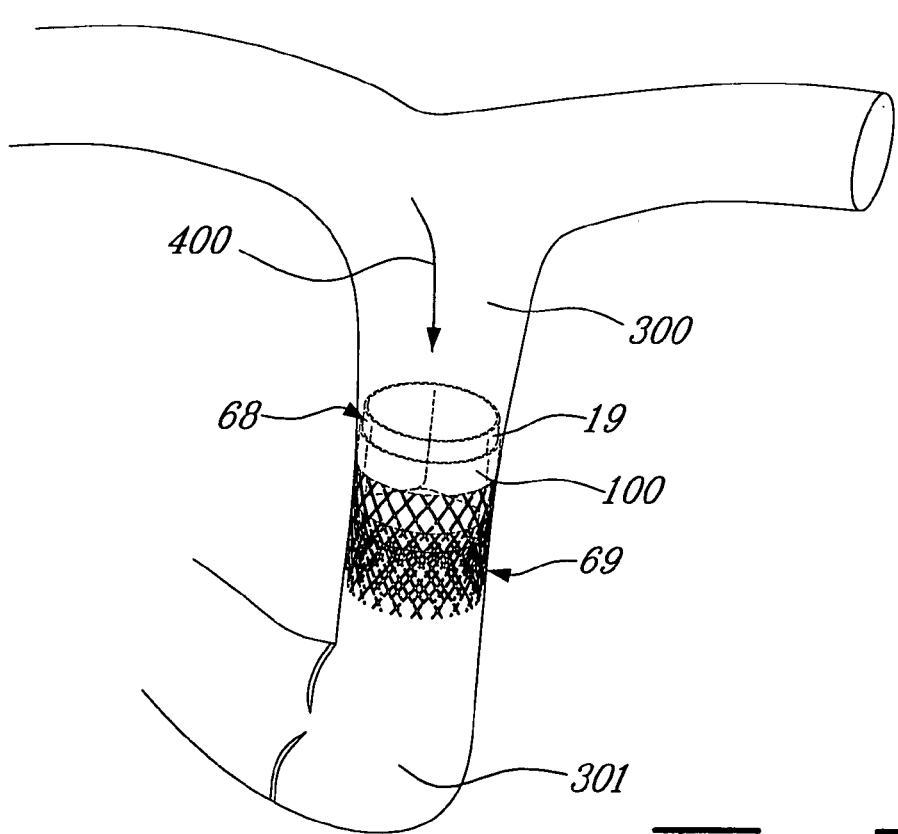
FIG_21B

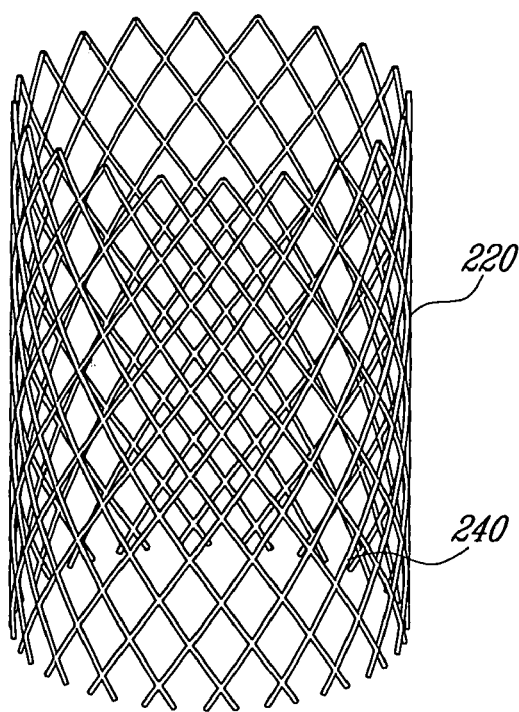# _FIG_22A
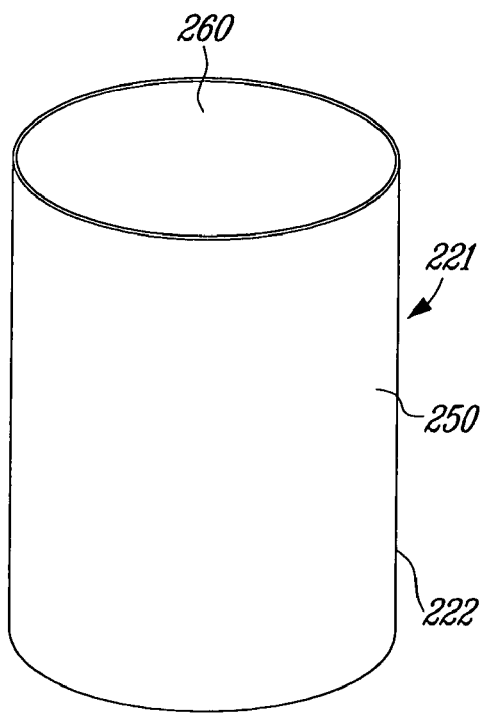# _FIG_22B
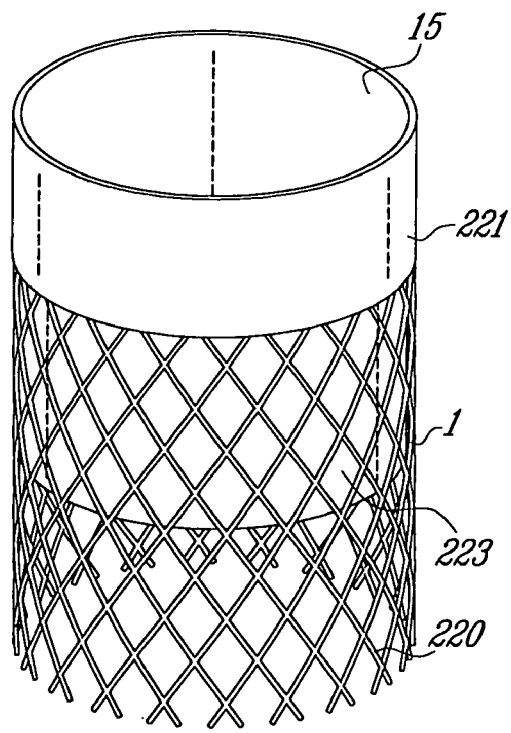# _FIG_22C
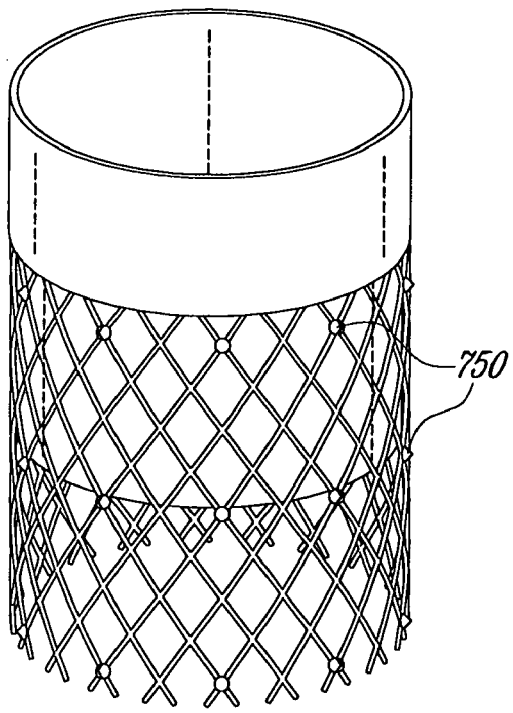# _FIG_23

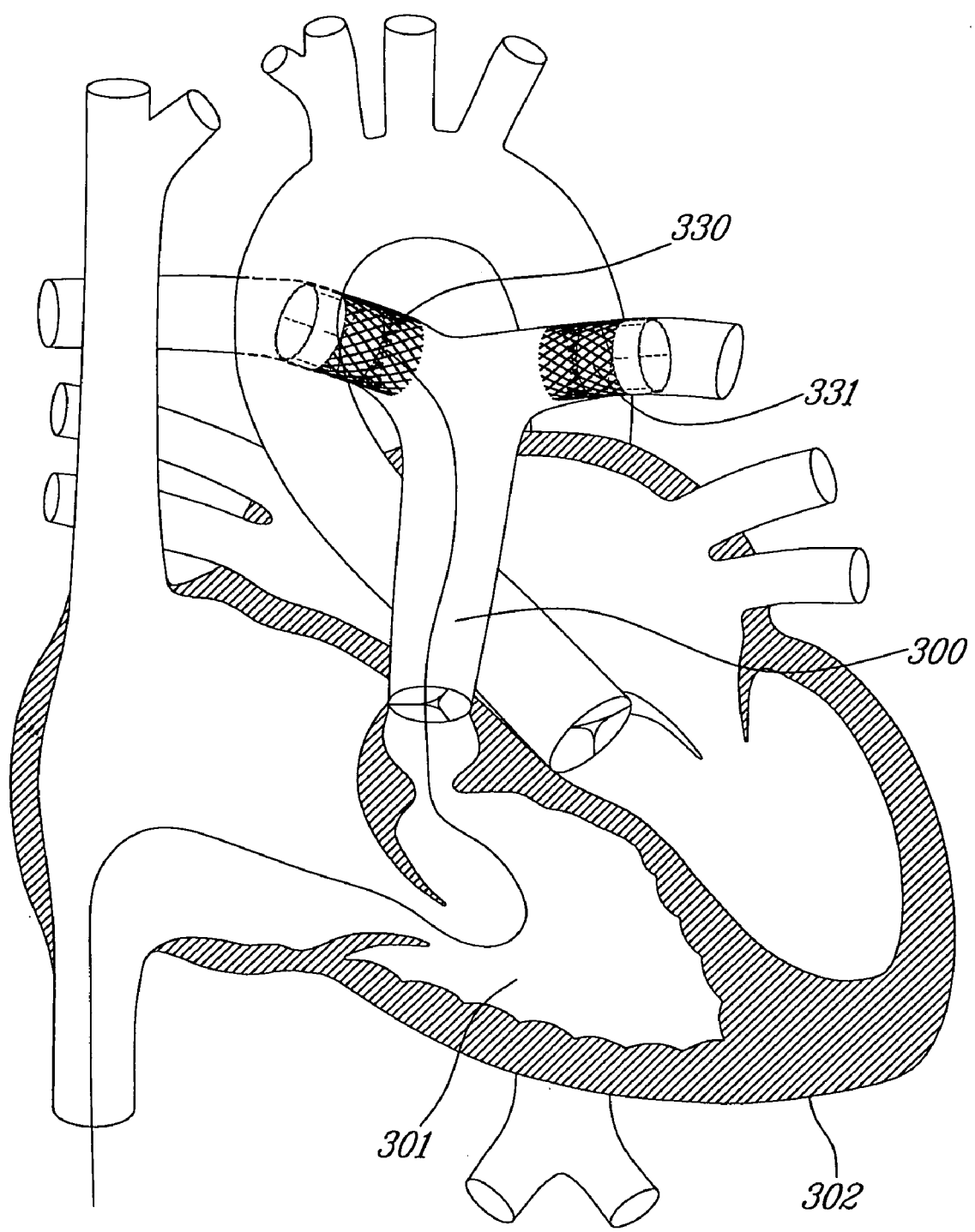
FIG_24

```
┌─────────────────────────────┐
│  EXPANDING THE FIRST PROSTHETIC   │─ 802
│  VALVE TO A PREDETERMINED DIAMETER │
│  SUCH THAT THE FIRST PROSTHETIC   │
│  VALVE CEASES TO FUNCTION AND AN  │
│  OPENING IS PROVIDED WITHIN       │
└─────────────────────────────┘
              │
              ▼
┌─────────────────────────────────────┐
│  INSERTING A SECOND PROSTHETIC VALVE │─ 804
│  HAVING A DIAMETER SUBSTANTIALLY EQUAL│
│  TO THE PREDETERMINED DIAMETER INTO  │
│  THE OPENING                         │
└─────────────────────────────────────┘
```

FIG. 25

```
┌─────────────────────────────┐
│  PROVIDING A FIRST PROSTHETIC │─ 806
│  VALVE IN A RIGHT PULMONARY   │
│  ARTERY ADJACENT TO THE MAIN  │
│  PULMONARY ARTERY             │
└─────────────────────────────┘
              │
              ▼
┌─────────────────────────────┐
│  PROVIDING A SECOND PROSTHETIC │─ 808
│  VALVE IN A LEFT PULMONARY     │
│  ARTERY ADJACENT TO THE MAIN   │
│  PULMONARY ARTERY              │
└─────────────────────────────┘
```

FIG. 26

STENT MOUNTED VALVE

FIELD OF THE INVENTION

The invention relates to the field of medical devices and, more specifically, to the field of prosthetic valves inserted percutaneously or surgically.

BACKGROUND OF THE INVENTION

The primary function of a valve is to ensure that a fluid flows only in one direction. There are many valves in the human body, helping to make sure that homeostasis is maintained in an efficient manner. There are four valves in the heart that regulate the direction and flow of blood. The pulmonary valve directs blood from the right ventricle into the main pulmonary artery where it flows into the lungs. The aortic valve directs blood towards the aorta, the main artery of the body. The mitral and tricuspid valves are internal to the heart, directing blood flow between the atria and ventricles. Valves may fail to function due to inadequate opening (also known as narrowing, or stenosis), inadequate closure (also known as leaking, or regurgitation or insufficiency), or a combination of both processes. The aortic valve is the one that most commonly fails in older adults. In children, the pulmonary and aortic valves are the ones that most often need to be repaired or replaced due to congenital defects.

Pulmonary insufficiency (regurgitation) can be a result of congenital heart disease. Typically this condition would be exhibited by patients who have had previous repair of Tetralogy of Fallot. Another indication would be insufficiency of a right ventricle-to-pulmonary artery conduit, also seen in Tetralogy of Fallot or pulmonary atresia with ventricular septal defect (VSD), and also after previous repair of truncus arteriosus.

The traditional way to replace cardiac valves in patients involves open-heart surgery. The patient must be placed under general anesthesia for several hours. The patient's sternum is cut open, and incisions are made through the various tissue layers and into the heart to expose the area of interest. A replacement valve is implanted. A cardiac bypass machine must be used to pump blood while the heart is stopped. This type of surgery causes significant trauma to the patient with prolonged healing times.

The replacement heart valves currently available for traditional open-heart surgery have both advantages and disadvantages. Mechanical valves are long lasting and durable, but may require a lifetime of anticoagulation (anti-clotting) treatment. The mechanism of closure may damage blood cells and platelets, as well, it may be audible to the patient. Biological valves, usually harvested from pigs or cows (eg. Bovine jugular veins), do not generally last as long as mechanical valves, as they tend to calcify and stiffen. Their advantage is that they do not require that patients take anticoagulation treatment. As well, with growing concerns over the possible spread of disease from animal tissues (eg. Mad cow disease), it would be ideal to avoid the biological tissues altogether. Children with congenital heart disease may require several operations over a period of years to correct multiple cardiac defects. Repeated surgical repair or replacement of cardiac valves places an additional burden on them.

A biological valve for surgical implantation is sometimes mounted into a support structure called a stent. This stent is a supportive material that is surgically sutured into the valve. A biological valve supported by a stent that is inserted surgically can be referred to as a stented valve. Biological valves can be stented valves or unstented valves.

The rapidly developing specializations of interventional cardiology and interventional radiology involve placing tools and devices deep into the body under imaging guidance through small incisions percutaneously("through the skin") into veins or arteries. These procedures are less invasive than traditional open-heart surgery, allowing the patient to recover more quickly. The procedures take less time to perform, are safer, and are generally less costly. Percutaneous technologies therefore benefit both the patients and the health care system.

Due to the benefits of percutaneous procedures over open surgery, there has been increasing interest in developing percutaneous methods of replacing heart valves. Prior art systems include valves that can be delivered and deployed percutaneously. Progress has been made with the designs, however none of the designs are ideal, each having important limitations.

Bonhoeffer is a researcher that has performed clinical trials on animals and humans. A pulmonary valve has been percutaneously implanted in several patients. The valve is composed of an 18 mm bovine internal jugular vein with a native valve that has been dissected and reduced in profile. The valve is mounted on an expandable stent, and loaded into a specially made 18 F sheath. The system is delivered over a guide-wire and deployed using an expandable balloon. This research has been documented in several scientific papers. The valve and stent are disclosed in European Patent Application No. 1057460.

There are many disadvantages to the Bonhoeffer valve. The main one is that a large sheath is required (18-22 F) for implantation of the valve, too large to be used in small children. Bonhoeffer employs biological material as his choice for the valve. Biological materials are known to have less durability. Biological valves experiences calcification after a relatively short time period and cease to function adequately. In addition, obtaining biological material and forming it into a valve is difficult and time consuming. The biological material must be treated chemically, in effort to improve longevity and to reduce the risk of disease transmission.

Cribier is another researcher, focusing on the percutaneous implantation of aortic valves in adults. The Cribier valve that has been used in patient trials was made of either bovine pericardium or equine pericardium. The stent was 14 mm in length, and was delivered on a balloon 30 mm in length with a maximal diameter of 23 mm. The delivery profile for the assembly is even larger than that of Bonhoeffer's at 24 F.

U.S. patent application Ser. No. 2003/0023300, World Patent Application No. 02/47575, and U.S. Pat. Nos. 6,440, 164 and 6,503,272 all disclose a percutaneously delivered non-biological valve mounted on a stent, which can also be referred to as a valve-stent. A main disadvantage of these designs is that the valve leaflets are supported by metal that is either an extension of the stent, or welded to it. The metal is expected to move into different positions, thereby opening and closing the orifice with each heartbeat. This will place considerable stress on the joint, potentially causing early failure of the valve due to metal fatigue.

Biological valves harvested from animals have benefits, and are therefore selected for many designs in the prior art. However, there are also many disadvantages to their use. Biological valves calcify and stiffen, which leads to deterioration in valve function over time. They require a large sheath size for introduction into the body, increasing the risk of vessel trauma in adults, and excluding their use in children. Finally, biological valves are difficult to work with. Each valve involves the slaughter of an animal, then a manual harvesting of the valve, careful chemical treatment, and hand assembly of the valve. The process is cumbersome, and labor intensive. U.S. Pat. Nos. 6,582,462, 6,425,916, 5,957,949 and World Patent Application No. 0047136A1 all disclose a biological valve as a preferred embodiment and suffer from the described disadvantages.

A healthy heart of an average human beats about 70 times a minute. This translates into approximately 600 million beats over a 15 year period, which is the FDA requirement for a mechanical heart valve. The FDA requirement for a biological heart valve is that it must last 5 years, or 200 million beats. Therefore, a heart valve must be designed and engineered to be rugged and durable. A general engineering principle is that simpler designs last longer, the smaller the number of components and parts, the lower the probability of component failure. Therefore, in designing a heart valve, the number of different materials, sutures and bonds should be minimized. United States Patent Application No. 20020198594A1 and World Patent Application No. 03047468A1 involve complex designs, with a large number of sutures and bonds, as well as different materials for the leaflets and stent graft.

U.S. Pat. No. 6,287,334 discloses a valve made out of synthetic bioprosthetic material. Three cone shaped cavities open and close with regards to the pressure differential of the fluid, thereby creating an opening in one direction, and closing in the other. This design features three independent cones, increasing the likelihood of valve dysfunction if one of the cones does not open in response to a change in pressure. This may occur if the material sticks to itself because of the adhesive attraction property of water. A second drawback to this design is that a cone is not a natural shape for a valve. Blood may pool at the bottom of the cone, stagnate, and form clots.

United States Patent Application No. 20030130729 seeks to solve the above problems by using only a biological material, and folding it in such a way as to create leaflets. The rectangular piece of biological material needs to be treated in a certain manner, dehydrated, folded and re-hydrated to achieve the desired result. The end result of the folding should be leaflets inside of a tube that is bonded or sutured to the stent. A problem with this design is that a suture line is created, where the two edges are connected to form a tube. This suture line interferes with the operation of the leaflets. It also acts as an opening for blood to seep into the space between the graft and artery, increasing the risk of clot formation.

U.S. Pat. No. 5,855,601 discusses a valve mounted on a stent, in which the leaflets and graft are formed from a single piece of material. Another embodiment is for the cusp to be secured to the outer side of the stent. If the first embodiment is selected, the leaflets may stick to the graft if both are made out of a synthetic plastic-like material. If the second embodiment is selected, then the leaflets on the inside will rub against the metal of the stent, thereby wearing out faster and reducing the life of the valve. In both embodiments, no mechanism is described for preventing the leaflets from inverting instead of closing with an alternating pressure differential. An inversion of leaflets is a hazardous situation, rendering the valve non-functional, and causing severe insufficiency.

United States Patent Application No. 20030109924 also seeks to solve the above problems, by using a continuous material to form a valvular structure that can deform to block the flow of fluid. The valvular structure collapses the same way each time along stiffened zones. The shape of the material is a truncated hyperboloid shape, the base is large, and ends in a smaller neck. A disadvantage of this design is that the orifice area is reduced. In fact, this patent acknowledges the smaller orifice area, and admits that this invention can only be used in elderly patients, as their cardiac output is lower.

SUMMARY OF THE INVENTION

Accordingly, an object of the present invention is to provide an entirely synthetic valve, manufactured out of a tube that is folded and bonded in a unique way to form leaflets which function as a valve.

Another object of the present invention is to provide a cardiac valve that is designed for pediatric use. Creation of a valve that is implantable in children is met with a set of even greater challenges than a valve designed for adults. First, the valve must be implanted through a much smaller delivery system. Second, although valve failure due to deterioration of the leaflet material is a universal concern for patients of all ages, the rapid body growth found in children means that a child may simply "outgrow" a valve even without deterioration in leaflet function (by virtue of an orifice which may become too small for a child after a period of rapid growth, despite proper leaflet mobility). A valve implanted in children should ideally be replaceable by percutaneous means once it has been outgrown. This may be accomplished by implanting a new (larger) valve within the original valve that has been outgrown.

Yet another object of the present invention is to provide a prosthetic valve that can be deployed percutaneously in a small child. This requires a design that can be collapsed into a sheath size of 12-14 F or smaller, to allow insertion into the small veins or arteries of children.

A further goal of the present invention is to provide a variety of valves with optimal diameters, for optimal implantation into different sized patients.

A further goal of the present invention is to provide a method to replace a worn or defective valve, or to replace a valve that the child has outgrown.

A further goal of the present invention is to provide an optimal number of leaflets such that the orifice area is maximized in the open state, and reverse flow of fluid is impeded in the closed state.

A further goal of the present invention is to overcome the adhesion attraction property of water.

A further goal of the present invention is to mimic as closely as possible the design and functionality of the native pulmonary and aortic valve.

A further goal of the present invention is to provide a mechanism that prohibits the leaflets from reversing.

A further goal of the present invention is to provide a method of attachment that will preserve the integrity of the leaflets as the stent is compressed, in preparation for deployment.

A further goal of the present invention is to be able to expand a stent with the valve mounted inside, the stent being crimped onto a balloon before delivery, without compromising the integrity of the valve.

A further goal of the present invention is to prevent formation of thrombus within the leaflets.

A further goal of the present invention is to provide hooks on the stent for preventing migration of the device in patients with high pressures distal to the prosthetic valve.

A further goal of the present invention is to separate the device from its delivery system (balloon, catheter, sheath), thereby allowing for flexibility to select an optimal selection of each component individually.

A further goal of the present invention is to utilize the advantages of both mechanical and biological valves without the disadvantages. For mechanical valves, this includes high durability. For biological valves, this includes preventing the formation of clots without taking anticoagulants, and not damaging blood cells and platelets as the valve is opening and closing. Biological valves also tend to calcify after a period of time, thereby hardening and ceasing to function. The present invention reduces the probability of this occurring.

A further goal of the present invention is to leverage the existing knowledge of interventional cardiologists and interventional radiologists. This invention builds upon the existing line of products and tools available, such as the use of fluoroscopy to guide catheters into position, insertion of balloons over a wire, and balloon expansion of stents.

A further goal of the present invention is to provide a mechanism to either promote or inhibit infiltration of the body's own cells. Infiltration of cells onto the valve material may be made more favorable by appropriate material selection, with a benefit that such a layer of cells may prevent formation of thrombus. Alternately, cellular ingrowth may be inhibited, thereby preventing excessive growth that may lead to impaired leaflet mobility.

The valve designs in accordance with the invention are directed towards combining various features that together, provide a more secure, more efficient valve that is easier to manufacture and more resilient. One preferred embodiment consists in making the valve out of a single tubular membrane. One advantage of doing this is to reduce the number of sutures required. Extra sutures/bonding may create functional problems for the valve, like extra spaces where blood can flow into. A single tube also simplifies the manufacturing process. Furthermore, the overall strength of the valve is improved by having a single tube because a single piece of material is stronger than two separate pieces of the same or different materials. In order to create the leaflets that form the valve from the single tube, an end of the tube is internally folded and bonded to itself at a plurality of points. Pouches are thus formed and include the leaflets.

Additionally, it has been found that blood may find itself between the artery and the graft of the valve, thereby leading to clotting. To prevent blood from entering this space, a sleeve is provided which extends over the end of the stent onto the outer surface of the stent. This sleeve also helps to support the valve during the point of maximum stress, when blood flow reverses and the valve closes. Moreover, it has been found that it is difficult and not practical to suture the graft directly to the stent, since the stent needs to be compressed a lot. It is better to suture through the stent using a material-material type of bond.

According to a first broad aspect of the present invention, there is provided a prosthetic valve to be inserted into a body lumen, the valve having leaflets that are spread apart during forward flow of fluid to create an orifice, and the leaflets coming into contact with each other during reverse flow of fluid, thereby impeding the reverse flow of fluid, the valve comprising: a hollow, cylindrical stent having an inner surface and an outer surface, and having a first and a second open end; and valve means formed from a single tubular membrane, the membrane mounted to the stent, the membrane having a graft portion internally folded and bonded to itself at a plurality of points to form pouches such that the leaflets extend from the pouches, and a sleeve portion on an outer surface of the stent to secure the membrane thereto.

Preferably, the sleeve does not extend beyond an upper half of the stent, and the leaflets are positioned about a lower half of the stent.

According to a second broad aspect of the present invention, there is provided a prosthetic valve to be inserted into a body lumen, the valve having leaflets that are spread apart during forward flow of fluid to create an orifice, and the leaflets coming into contact with each other during reverse flow of fluid, thereby impeding the reverse flow of fluid, the valve comprising: a hollow, cylindrical stent having an inner surface and an outer surface, and having a first and a second open end; and a tubular membrane mounted to the stent, the tubular membrane having a graft portion within the stent internally folded and bonded to itself at a plurality of points to form pouches such that the leaflets extend from the pouches, and wherein the pouches are interconnected such that fluid entering a first of the pouches can flow into an adjacent pouch during the reverse flow of fluid to fill the adjacent pouch and cause all of the leaflets to come into contact for impeding of the reverse flow.

According to a third broad aspect of the present invention, there is provided a prosthetic valve to be inserted into a body lumen, the valve comprising: a membrane having a plurality of flexible leaflets that are spread apart during forward flow of fluid to create an orifice, the leaflets coming into contact with each other during reverse flow of fluid, thereby impeding the reverse flow of fluid, and at least one of the plurality of leaflets having a perforation therethrough to allow a small amount of regurgitation to be present during the forward and reverse flow of fluid, the perforation being positioned on the at least one of the plurality of leaflets such that the fluid is prevented from stagnating in a zone with a high risk of fluid stagnation.

Preferably, the prosthetic valve further comprises a stent having an inner surface and an outer surface, and having a first and a second open end, wherein said leaflets are mounted to said inner surface of said stent. The membrane may be a single tubular membrane and comprise a graft portion within the stent internally folded and bonded to itself at a plurality of points to form pouches including the leaflets, and the perforation is at a base of at least one of the pouches.

According to a fourth broad aspect of the present invention, there is provided a method of replacing a first expandable prosthetic valve percutaneously, the first prosthetic valve having a stent that can be re-expanded to a larger size and valve material that is stretchable beyond its usual dimension, the method comprising: expanding the first prosthetic valve to a predetermined diameter such that the first prosthetic valve ceases to function and an opening is provided within; and inserting a second prosthetic valve having a diameter substantially equal to the predetermined diameter into the opening such that the second prosthetic valve matingly engages and seals against the first prosthetic valve.

According to a fifth broad aspect of the present invention, there is provided a method of percutaneously replacing a non-functional valve in a main pulmonary artery, the method comprising: providing a first prosthetic valve in a right pulmonary artery adjacent to the main pulmonary artery; and providing a second prosthetic valve in a left pulmonary artery adjacent to the main pulmonary artery.

According to a sixth broad aspect of the present invention, there is provided a prosthetic valve to be inserted into a body lumen, the valve having leaflets that are spread apart during forward flow of fluid to create an orifice, and the leaflets coming into contact with each other during reverse flow of fluid, thereby impeding the reverse flow of fluid, the valve comprising: a hollow, cylindrical stent having an inner surface and an outer surface, and having a first and a second open end; and a tubular membrane mounted to the stent, the membrane folded to form the leaflets within the stent and having a sleeve portion on an outer surface of the stent to secure the membrane thereto, the leaflets having a base along a fold of the membrane, wherein the base of the leaflets is held along a circumference of the stent.

Preferably, the stent is between the sleeve portion and the leaflets at the base of the leaflets, and the membrane within the stent is bonded to the sleeve portion through a wall of the stent at a plurality of points to form the leaflets.

BRIEF DESCRIPTION OF THE DRAWINGS

These and other features, aspects and advantages of the present invention will become better understood with regard to the following description and accompanying drawings wherein:

FIG. 1 is a perspective view of the valve in its expanded state;

FIG. 2 is a top view of the valve fully open, allowing blood to pass through it;

FIG. 3 is a top view of the valve fully closed, impeding blood from flowing in reverse direction;

FIGS. 8a-f are illustrations of the formation of a sleeve, graft and leaflets;

FIG. 10 is a cross-sectional view of the valve in the closed position illustrating the impedance of blood flow;

FIG. 11 is a cross-sectional view of the valve in the open position illustrating the flow of blood through it;

FIG. 19 is an illustration of the deployment method of the present invention;

FIG. 21 is an illustration of a scenario in which the present invention is expanded and a second device inserted inside the first;

FIGS. 22a-c are perspective views of the primary components of the device;

FIG. 23 is an illustration of hooks placed on the stent;

FIG. 24 is another illustration of a possible deployment method of the present invention;

FIG. 25 is a flow chart of a method according to the invention; and

FIG. 26 is a flow chart of another method according to the invention.

DETAILED DESCRIPTION OF THE PREFERRED EMBODIMENT

Figure 4:
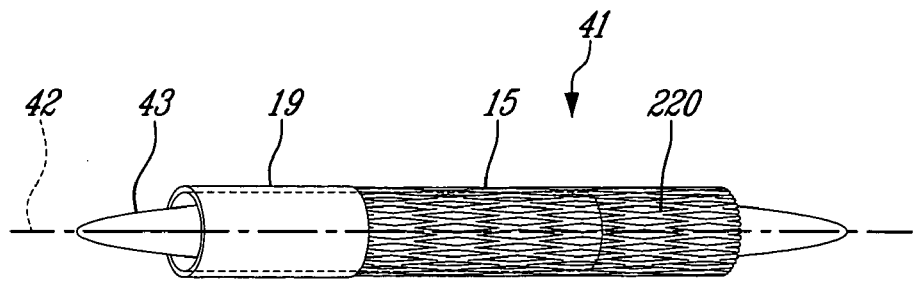
FIG. 4 is a perspective view of the device crimped on a balloon, before percutaneous insertion into a lumen.

In accordance with an aspect of the invention, preferred embodiments of a prosthetic valve are provided. It should be understood that throughout this application, the term "prosthetic valve" is used to mean any valve, whether implanted surgically or percutaneously, which is not a completely naturally occurring valve. This includes mechanical valves, biological valves made from living tissues, and polymer valves which combine features from both mechanical valves and biological valves.

The replacement of the pulmonary valve in a small child will be discussed in detail as an example. However, it should be understood that the present invention is not limited to this valve, and may be used to replace any of the cardiac valves, any venous valves, or any other valves in the body. As well, this invention can be used to establish valves in the body where no natural valves exist. For example, valves can be placed in the branch pulmonary arteries in patients where the main pulmonary artery is too short or too wide. In addition, this invention is not limited to small children. The same device and method can be used to replace valves in adults. A small child is discussed because the problems that need to be overcome are more complex, and thereby cover the adult case as well. Children with congenital cardiac malformations who had surgical pulmonary valvectomy or transannular pulmonary patches may experience pulmonary insufficiency that may lead to right ventricular failure.

A prosthetic valve 1 in accordance with a preferred embodiment of the invention is composed of two primary elements, a stent 220 and material 221 in the shape of a tube 222. Material 221 is a membrane, i.e. a thin and pliable layer of tissue, whether synthetic or biological, that is membrane-like for its physical properties. The tube 222 can be formed by taking a sheet material and folding it into a cylinder of a desired diameter. Alternatively, a material already having a tubular shape may be used, such as biological tissue taken from a vein. The tubular structure may also be formed by injection molding. These elements are illustrated in FIG. 22a and FIG. 22b. The stent 220 and the material 221 are bonded together in a unique way to form the prosthetic valve 1 as pictured in FIG. 22c. The method of the formation of the valve, bonding the material 221 to the graft 15 to form a valve 223 will be discussed in more detail.

This system requires a stent with specific properties. Stents 220 have found many uses in interventional medicine recently, from treating coronary artery disease, to treating coarctation of the aorta. The stent 220 that will be expanded to anchor the valve 223 described in this invention into place must meet several criteria. The maximum expandable diameter of the stent 220 should be 26 mm, but not limited to it. Currently only a small number of stents exist with this capability. Most notable are the Palmaz P3110, P4010, and P5010 Stents by Cordis. The Palmaz Stent can expand to 26 mm in order to treat stenoses in large vessels such as the aorta and pulmonary arteries. The term stent is to be understood as meaning any known medical stent, a metal scaffold, a non-metal scaffold such as a plastic tube, or any type of non-perforated cylindrical support structure. The stents used can be collapsible or not, balloon-expandable, or self-expandable. The stent 220 must have high radial strength once expanded, in order to anchor the valve 223 securely. To save a second surgery on a growing child, a second prosthetic valve 68 can be implanted inside of a small or defective first prosthetic valve 69. If a second prosthetic valve 68 is implanted inside the first prosthetic valve 69, the second prosthetic valve 68 must be able to stay secure. If the first stent needs to be expanded a second time in order to accommodate the implantation of a second stent inside the first one, as in the above case, it should not be made out of a memory material such as Nitinol. Nitinol or other self-expanding memory metals that have become highly popular in recent years are not ideal materials for pediatric applications, as they only take on a single diameter. These materials are designed for fully-grown adults with a constant artery size. For adults, both traditional elastically deformable materials and memory metals are suitable materials for a stent. It should be noted that currently available memory metals do not have the same radial strength as balloon expandable steel stents. The preferred material for the stent is Steel 316L, but not limited to it. It is preferable that the stent 220 should be balloon expandable, as this allows for careful sizing and control over the expansion diameter. Balloon expansion is well known in the art, and practiced by interventional cardiologists and interventional radiologists. The stent 220 made out of steel or any other suitable material crimped over an expansion balloon 43 is preferred. The stent 220 can be expanded multiple times, as is common practice to expand stents in children as their vessels grow. A second embodiment of the present invention is the use of a memory metal for the stent 220. The use of a memory metal requires a different delivery system and method, as a balloon is not required for expansion. The stent size is pre-selected, and the stent 220 self-expands to that diameter once it is deployed.

In order to accommodate and support a valve 223 in the heart, a stent length for a preferred embodiment in accordance with the invention should be between 2 and 5 cm. In addition, it must not have any sharp edges that may puncture the material 221 or the expansion balloon 43. Finally, the prosthetic valve 1 should compress to a preferred size of 4 mm or less, so that it can fit into a 12 F sheath. However it should be noted that other sizes may be selected.

This invention proposes to link the best of the two valve categories: mechanical and biological. An embodiment of this invention comprises a completely synthetic valve 223, classifying it as mechanical, as it is extremely durable. However, the design goal is to mimic the natural pulmonary and aortic valve, thereby providing the benefit of avoiding the formation of clots, and damage to blood cells and platelets.

A further embodiment of the present invention is to select a biological material for the tube 222. A most suitable biological material will be already in the form of a tube 222, for example a vein. The method of the formation of the valve is similar to the one described for synthetic materials. The bonding method in the formation of the valve will differ, as the biological material is different than bio-compatible synthetic material. Bonding techniques known in the art include glue, sutures, or other methods. The formation of a valve 223 using the described method will allow the prosthetic valve to be compressed to a small profile for introduction into veins and arteries of children. Another advantage is that a single sacrificed animal may be able to yield more than one valve. It is important to note the distinction between this invention and previous art. This invention describes the use of a tube 222 that is folded to form leaflets 100 and bonded to yield a valve 223. Previous art describes obtaining a bovine jugular vein or other naturally-existing valve fully intact (therefore leaflets and valve are fully formed and pre-existing in the animal). The profile of a pre-existing valve would conceivably be much larger, as well as having several other disadvantages previously discussed.

FIG. 1 illustrates a preferred embodiment of the prosthetic valve 1. The material 221 forms a sleeve 19 over the stent 220. The material 221 attached to the inside of the stent 220 shall be referred to as a graft 15. The graft 15 and the sleeve 19 are attached together through trans-stent-wall bonds 14. Additional material-material bonds 16 are used to form leaflets 100 from the material 221, after the graft 15. The prosthetic valve 1 is placed inside a body lumen that experiences a pressure differential. For example, the prosthetic valve 1 can be used to replace the native pulmonary valve. In this example, proximal end 13 is pointing towards the right ventricle 301, and distal end 12 points towards the main pulmonary artery 300. During systole, when the right ventricle 301 contracts, the pressure inside it rises above the pressure in the main pulmonary artery 300. Blood is forced from the proximal end 13 to the distal end 12. FIG. 2 illustrates how the prosthetic valve 1 functions under this condition. The leaflets 100 are forced towards the graft 15 attached to the inside of the stent 200, creating a large orifice 25 for the blood to flow through. During diastole, the pressure in the right ventricle 301 falls below that of the main pulmonary artery 300. Blood begins to reverse direction and travel from the distal end 12 to the proximal end 13. FIG. 3 illustrates the leaflets 100 under this condition. The blood is caught by the leaflets 100, forcing them to move away from the graft 15. The leaflets 100 come in contact with one another, thereby impeding the reverse flow of blood 400. FIGS. 10 and 11 are sliced side views of a preferred embodiment of the present invention. FIG. 10 illustrates the prosthetic valve 1 in a position where the reverse flow of blood 400 is impeded by the leaflets 100. FIG. 11 illustrates the prosthetic valve 1 in a position where the forward flow of blood 410 is not impeded. The leaflets 100 are pushed towards the graft 15.

FIG. 4 illustrates how the prosthetic valve 1 is crimped on a balloon 43, ready to be delivered over a wire 42, thereby forming a complete system ready for percutaneous insertion 41. The sleeve 19 and graft 15 are compressed by the stent 220.

Several prosthetic valves 1 will be manufactured, each optimized to work at a specified diameter. The preferred embodiment is to manufacture diameters as follows (in mm): 10, 12, 14, 16, 18, 20, 22, 24, 26 for use in the aortic or pulmonary position, but other sizes could be manufactured to accommodate other structures in the body requiring a valve implant.

The valve 223 described will have leaflets 100 made out of a bio-compatible synthetic material. The preferred material to use is ePTFE, expanded polytetrafluoroethylene (marketed as Gore-TEX by Gore & Associates). The pore size of Gore-TEX can be specified. There are two categories. The first is a pore size that is so small that it excludes all cell ingrowth. This has the benefit of reducing the risk that the growing cells will cause the leaflets to stick. The second embodiment is Gore-TEX with a sufficiently large pore size that allows the ingrowth of cells. The advantage of a cell layer is that it prevents the formation of thrombus, as well as protecting blood cells and platelets from mechanical damage. If the leaflets are fully covered with cells, they should function similarly to a natural pulmonary valve. The preferred embodiment is to exclude all cell growth to provide the prosthetic valve 1 with maximum durability.

Figure 5:
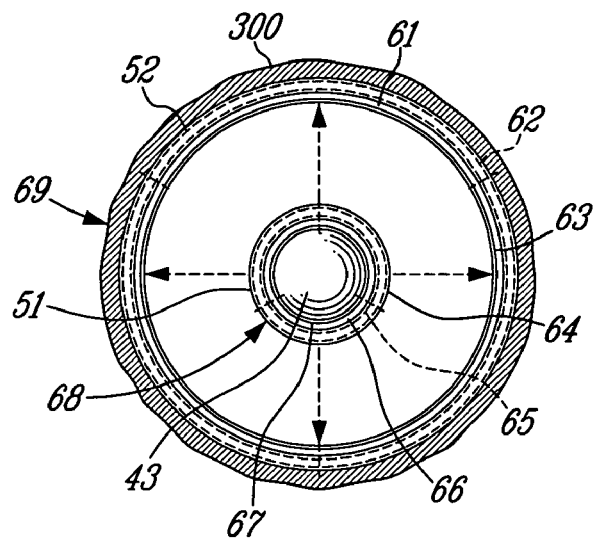
FIG. 5 is a top view of the device being expanded from functional diameter to maximum dilation diameter.

The bio-compatible synthetic material 221 needs to be flexible and stretchable. FIG. 5 illustrates the need for this prosthetic valve 1 requirement. The prosthetic valve 1 needs to function at a first diameter 51, which can equal to the preferred minimum value of 10 mm (for example). Once the child reaches adulthood, the diameter of the main pulmonary artery 300 can be as large as a maximum stent diameter of 26 mm. The preferred embodiment is to insert an expansion balloon 43 into the first prosthetic valve 69 and expand it to a second diameter 52, the diameter of the main pulmonary artery 300. The expansion balloon 43 expands inside the first prosthetic valve 69, stretching out the bio-compatible synthetic material 221. The valve 223 ceases to function, as the leaflet 100 edges can no longer touch each other and therefore no longer impede the reverse flow of blood 400. A second prosthetic valve 68 designed to work at the expanded second diameter 52 can now be inserted and expanded inside the first prosthetic valve 69.

Figure 6:
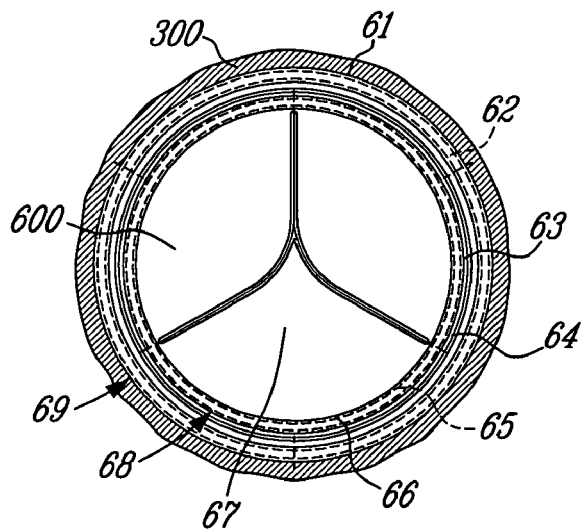
FIG. 6 is a top view of a new device inside of a stretched pre-deployed device.

FIG. 6 illustrates the combined prosthetic valve sandwich that is formed. The main pulmonary artery 300 forms the outer barrier. Against the main pulmonary artery, the sleeve 61 of the first valve stent is shown pressed. Immediately adjacent and sequentially inward, the stent 62 of the first prosthetic valve followed by the stretched compressed leaflets 63 of the first prosthetic valve are illustrated. Next, the sleeve 64 of the second prosthetic valve, the stent 65 of the second prosthetic valve, and the graft 66 of the second prosthetic valve are shown. The leaflets 67 of the second prosthetic valve are designed to work at the new diameter, and are illustrated in the position in which they impede the reverse flow of blood 400.

The method in accordance with this aspect of the present invention is shown in FIG. 25. The first prosthetic valve is expanded to a predetermined diameter such that it ceases to function and an opening is provided within 802. A second prosthetic valve having a diameter substantially equal to the predetermined diameter is then inserted into the opening 804. This method can also be employed to replace a damaged prosthetic valve. It should be understood that although the preferred embodiment is to insert an expansion balloon into the first prosthetic valve while already having a second prosthetic valve mounted thereon, other embodiments are possible. For example, an expansion balloon may be inserted into the first prosthetic valve, the first prosthetic valve is expanded by inflating the balloon, the expansion balloon is removed, and a second prosthetic valve is mounted onto the expansion balloon in a collapsed format. The expansion balloon is then re-inserted into the opening that was previously created and the second prosthetic valve is expanded therein. Alternatively, the second prosthetic valve may be self-expandable and therefore not require the expansion balloon to be deployed. Also alternatively, the expansion balloon may not be required at all if the self-expanding and collapsed second prosthetic valve is inserted into the first prosthetic valve before the first prosthetic valve is expanded and the second, self-expandable prosthetic valve is used to expand the first prosthetic valve.

A requirement for this method is that the first prosthetic valve have a stent that can be re-expanded to a larger size than that at which it functions. Therefore, the stent is ideally not made of a memory-metal such as Nitinol and should not be at maximum diameter. Also required is that the valve material of the first prosthetic valve be stretchable beyond its usual dimension, so that the leaflets can be collapsed against the stent and an opening large enough to accept the second prosthetic valve be provided.

When using this replacement method, the direction of access to the valve for implantation of the second valve is ideal in the direction of blood flow, but not necessary to successfully perform the method. When advancing percutaneously against the flow, the first prosthetic valve opens with every heart beat and therefore provides the opening necessary to insert either an expansion balloon or a second prosthetic valve therein.

The bio-compatible synthetic material selected should be sufficiently thin, in order to allow for a minimal profile. The preferred bio-compatible synthetic material is ePTFE with a thickness of 0.1 mm, and with a pore size of less than 1 micron. The bio-compatible synthetic material should also be smooth so as not to cause unneeded turbulence in blood flow. It should not crease, kink or tear. In accordance with one embodiment, the tube is made from a sheet that is folded into a tubular form and the ends of the sheet are bonded together to close the tube. In order to ensure that the tube is of uniform thickness around its entire circumference, the sheet may be rolled such that the entire circumference of the tube has a double thickness of the material. In this case, glue is applied to the entire surface of the sheet instead of only at the point of contact between the two ends of the sheet.

The number of leaflets must be selected carefully. The leaflets 100 must fulfill several requirements; they need to be able to be delivered in a compressed state with a minimum profile, they must close tightly against each other to impede the reverse flow of blood 400, and they need to open to a large enough orifice 25 to allow for adequate forward flow of blood 410.

Figure 7A:
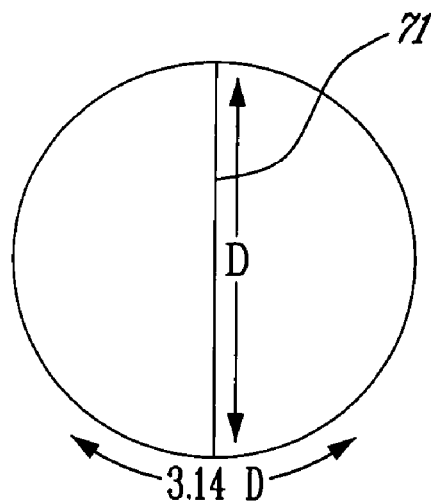
FIGS. 7a-d are illustrations of the optimal selection of 3 leaflets.
Figure 7B:
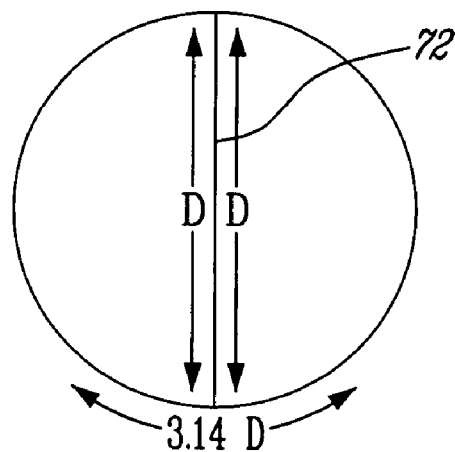
Figure 7C:
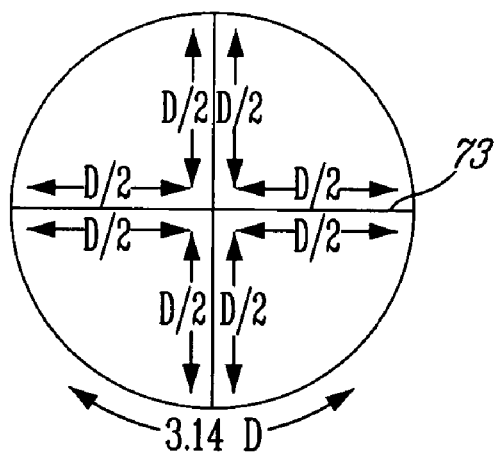
Figure 7D:
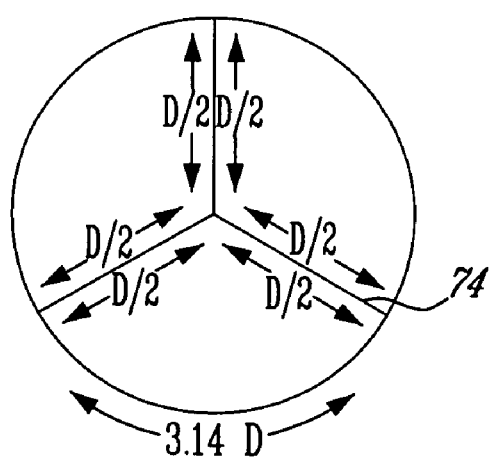

FIGS. 7*a-d* illustrate why choosing three leaflets is the optimal solution. To operate optimally, the sum of the length of the leaflets that are in contact should be very close to the internal circumference of the stent 71. For leaflets flush against the inside of the stent, the most efficient total edge length is (3.14) D, or simply the internal circumference of the stent 71. This will be the case if the leaflets 100 are formed from a tube 222 as in the case of the present invention. FIG. 7*b* illustrates the two leaflet case in which the sum of the length of the leaflets that are in contact is 2D 72. This leaves an excess of material as slack when the leaflets are in a closed position. For a four leaflet scenario, the sum of the length of the leaflets that are in contact 73 is 4D. Because only 3.14D is available, not all the leaflet edges will touch. For a three leaflet case, the sum of the length of the leaflets that are in contact 74 is 3D, which leaves only about a 5% mismatch with the diameter length.

Figure 8D:
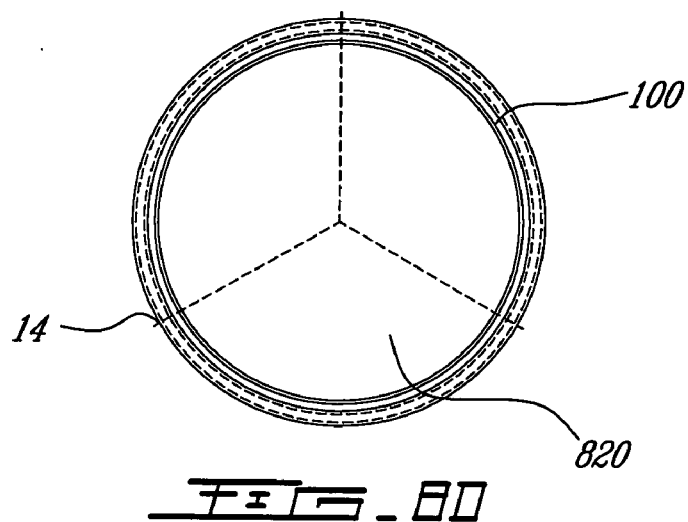
Figure 8E:
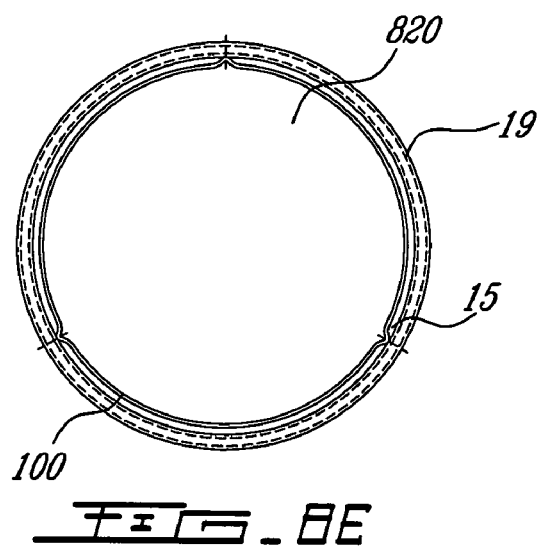
Figure 8F:
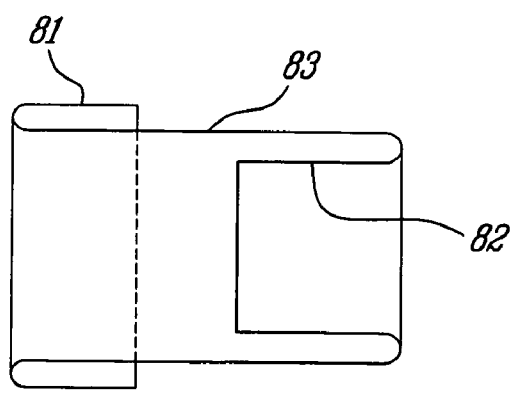

FIGS. 8*a-f* illustrate the formation of the leaflets 100, sleeve 19 and graft 15. The leaflets 100, sleeve 19 and graft 15 are all made out of a single tube 222 of material 221. Two ends A 81 and B 82 are folded over, but to opposite sides of the tube 222. The fold length A 81 is folded to the outer side of the tube 250, forming a sleeve 19. It is preferable to have a sleeve 19, as it provides extra support for the leaflets 100, and helps to adhere them to the stent 220. In addition, the sleeve 19 helps prevent blood from entering the space between the graft 15 and the wall of the main pulmonary artery 300, where it can stagnate and clot. A second embodiment is not to form a sleeve if suitable bonds are used to join the tube 222 directly to the stent 220. The leaflets 100 are comprised of fold length B 82, and the graft 15 is section C 83. Section B 82 is folded such that it is positioned inside the tube 222. The total length of the tube 222 in relation to the length of the stent 220 determines the position of the valve inside the stent. The valve 223 can be positioned approximately in the middle of the stent, or towards one of the ends by varying the length of C 83. In the first case illustrated by FIG. 8*b*, the length of C 83 is such that the leaflets 100 are approximately in the middle as related to reference stent length 88. In the second case as illustrated by FIG. 8*c*, the leaflets 100 are displaced toward the end of the reference stent length 88. The preferred embodiment is to place the leaflets 100 towards the end of the stent 220, to minimize the amount of extra metal of the stent that is not actively employed. As well, children usually have a short main pulmonary artery 300, therefore the prosthetic valve 1 needs to be short to fit without entering the heart 302 or blocking the branch arteries 303. The leaflets 100 are formed by using material-material bonds 16 between B 82 and C 83. FIG. 8*d* is a top view illustrating that the material-material bonds 16 are made equidistant or 120 degrees from each other to form 3 sections 820 that are in fact the leaflets 100. The length of 81 A can have a maximum length of the entire stent 220 length. The length of A 81 should be selected such that it is secure. Length A is folded to the outside of the tube 222, and using a trans-stent-wall bond 14, it is bonded to the graft 15 on the inside of the tube 222 through the stent 220 using any of a variety of techniques to form a sleeve 19. FIG. 8*e* and 8*f* illustrate the relative positions of the leaflets 100, sleeve 19 and graft 15 through a top view and a side view. It can also be appreciated that the tube with the sleeve and the internally folded portion forming the leaflets can be made using injection molding techniques well known in the field of injection molding.

Figure 9C:
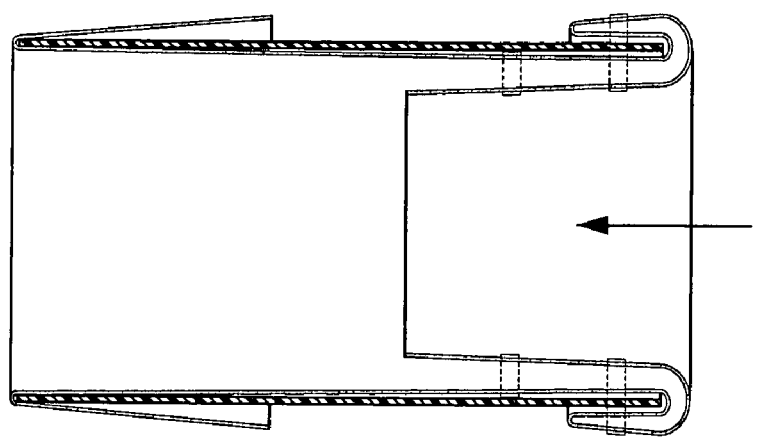
FIGS. 9a-c are front views of different embodiments showing the valve with the base of the leaflets held along a circumference of the stent.
Figure 9B:
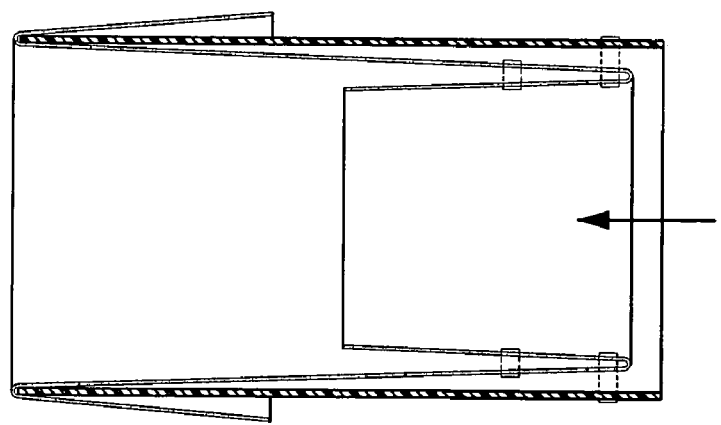
Figure 9A:
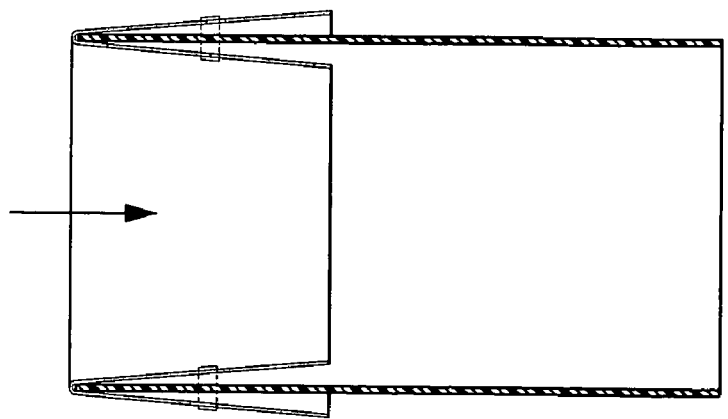

An alternative design to that proposed in FIG. 8 is shown in FIGS. 9*a* to 9*c*. In all three embodiments shown in FIG. 9, the membrane is folded to form the leaflets within the stent. A sleeve portion is on an outer surface of the stent to secure the membrane thereto. The leaflets have a base along a fold of the membrane and the base of the leaflets is held along a circumference of the stent In FIG. 9*a*, the stent is sandwiched between the sleeve and the leaflets up to the base of the leaflets. As indicated by the arrow, the forward flow of fluid will cause the Leaflets to move away from each other and towards the stent. The reverse flow of fluid will cause the leaflets to come into contact with each other and impede the flow of fluid. The membrane within the stent is bonded to the sleeve on the outer surface of the stent to form the leaflets.

In FIG. 9*b*, the membrane within the stent is inverted and bonded to itself to form the leaflets. The stent is between the sleeve and the membrane, but not at the base of the leaflets. However, the base of the leaflets is bonded to the stent around the circumference of the stent in order to prevent the leaflets from reversing during the forward flow of fluid, so as not to block the fluid from passing through the valve.

In FIG. 9*c*, the base of the leaflets is extended to the bottom end of the stent and a second sleeve, or cuff, is formed by reversing them over the end of the stent. This portion is then bonded either to the stent or to the portion of the membrane that is within the stent via a trans-stent-wall bond.

The stages of operation of the prosthetic valve 1 during the cardiac cycle are illustrated in FIG. 10 and 11. The graft 15 portion of the bio-compatible synthetic material protects the leaflets 100 from wear and tear. The leaflets 100, pushed apart by blood, lie against the graft 15, which is made out of the same material 221 as the leaflets 100. The leaflets 100 never touch the metal of the stent 220, thereby prolonging their durability, in the case of the embodiment described in FIGS. 9B and 9C.

Figure 12:
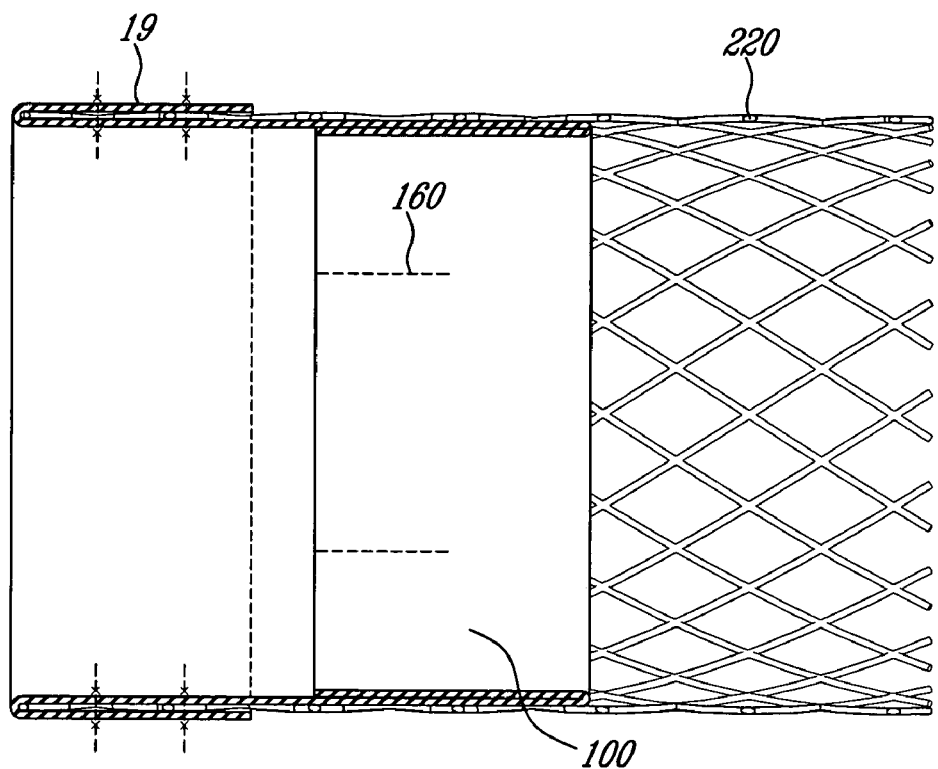
FIG. 12 is a cross-sectional view of the valve illustrating a preferred embodiment for the formation of leaflets.
Figure 13A:
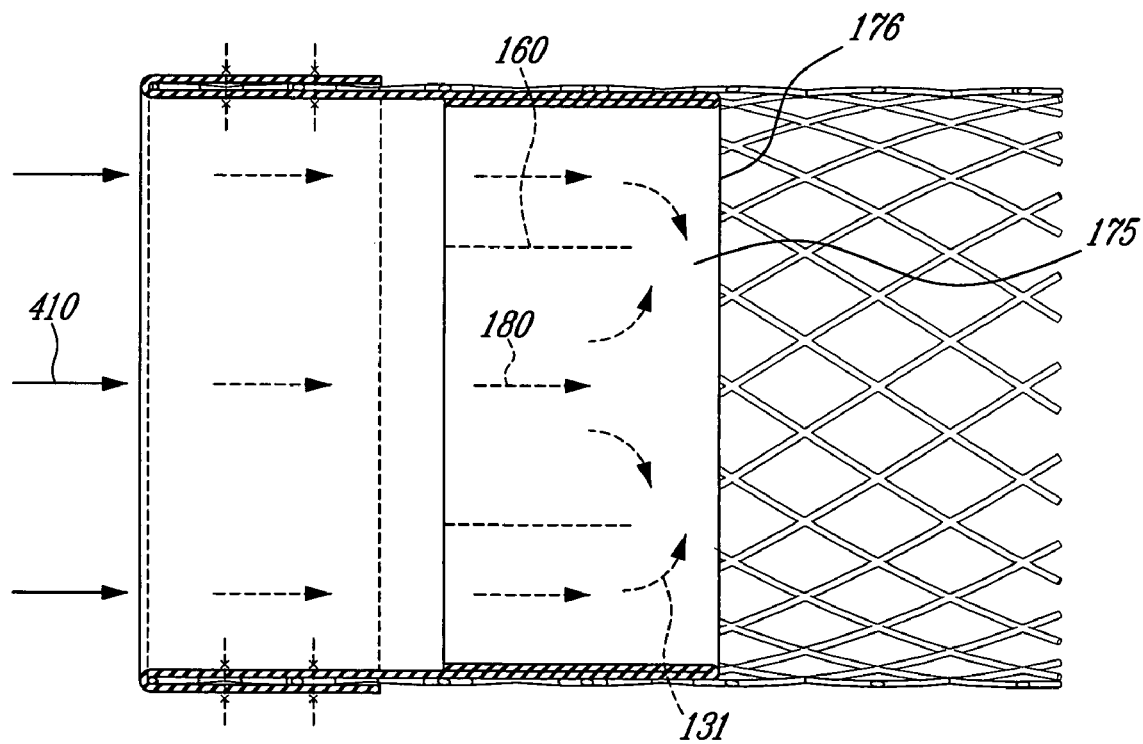
FIGS. 13a-b are cross-sectional views of the valve illustrating the advantage of the preferred embodiment for formation of the leaflets.
Figure 13B:
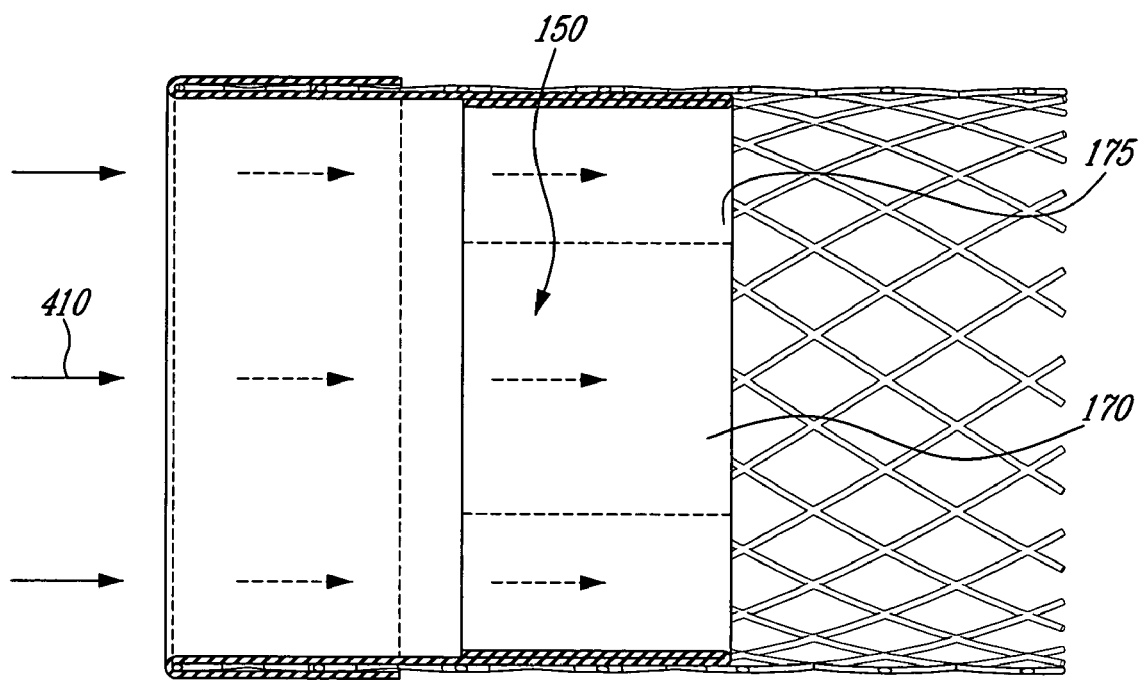

The material-material bonds 16 used to form the leaflets 100 can be in the form of sutures, glue or any other method known in the art. The material-material bonds 16 can take the full material-material bond length 150 of segment B 82, or a partial material-material bond length 160 such as a preferable length of half, as illustrated in FIG. 12. FIG. 13*a*-*b* illustrate the difference between a full material-material bond length 150 and partial material-material bond length 160. A full material-material bond length 150 will isolate each leaflet from its neighboring leaflet, creating isolated pouches 170. The reverse flow of blood 410 will only be able to fill up the isolated pouches 170 into which it enters. The disadvantage to this design is that one of the leaflets may become stuck to the graft 15. This may occur because of the adhesive property of water (a property related to capillary action). The chemical nature of water is to bond to itself and to smooth surfaces. If all three of the leaflets 100 do not come in contact, blood will be able to flow in reverse 410, thereby creating insufficiency. FIG. 13*a* is an illustration of a preferred embodiment of the present invention in which the bond length that forms the leaflets is a partial material-material bond length 160. Interconnecting the leaflets by leaving some segment unbonded provides continuity between the leaflets. Therefore even if one or two leaflets 100 get stuck to the graft 15, blood can flow from the open pouch to the pouch or pouches which have remained closed 131 and cause them to open. (There is one open pouch, two closed pouches in this example).

An advantage of the present invention over previous art is that the likelihood of the leaflets 100 inverting in direction and thereby destroying the functionality of the valve 223 is greatly reduced. As the leaflets 100 are made from a tube 222 of bio-compatible synthetic material 221 that has a partial material-material bond length 160 or a full material-material bond length 150, they are supported in such a way that inversion of the leaflets is improbable.

Figure 14:
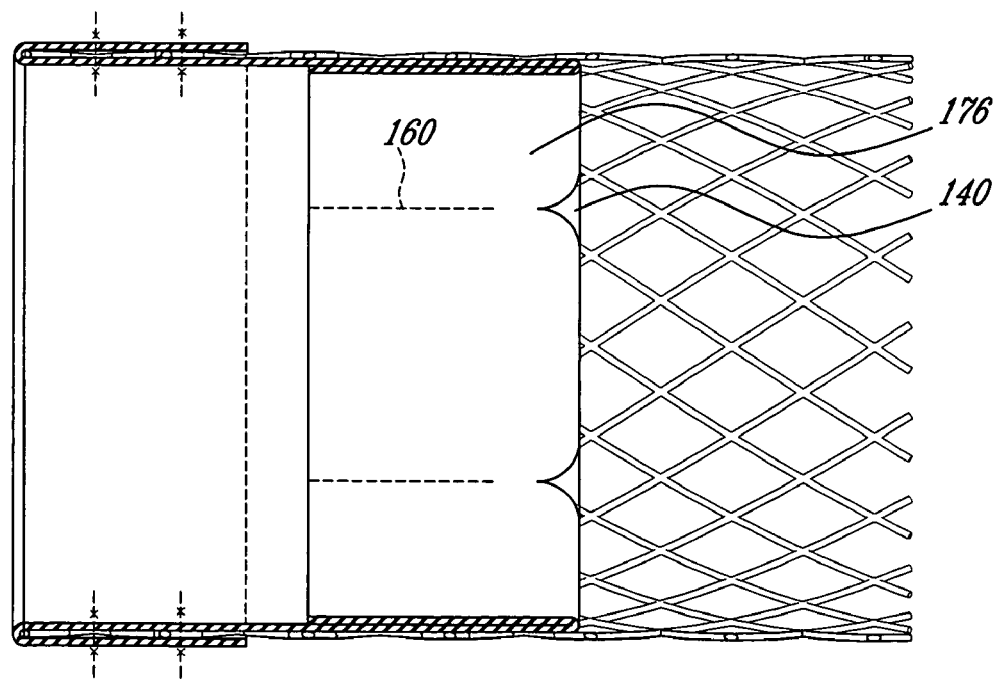
FIG. 14 is a cross-sectional view of the valve illustrating another preferred embodiment for formation of the leaflets.

A simple folding of segment B 82 creates a squaring off of the bottom of each pouch, creating a ninety degree angle 175. This may not be an optimal design, as the abrupt ninety degree angle 175 leaves an area where blood may stagnate. This pool of stagnant blood can lead to the formation of thrombus. The problem may become more pronounced if a full material-material bond length 150 of segment B 82 is chosen. To circumvent this issue, the partial material-material bond length 160 of fabric segment B 82 that forms the leaflets 100 may need to be connected in such a way that the transition from the partial material-material bond length 160 to the base of the leaflets 176 is done gradually, and not abruptly in a ninety degree angle 175. FIG. 14 illustrates the preferred embodiment of the present invention in which the base of the leaflets 176 is scalloped or tapered 140, thereby eliminating the ninety degree angle 175. This can be accomplished using a bond to scallop the base of the leaflet 176. Glue, or any other methods known in the art can also be used.

Figure 20A:
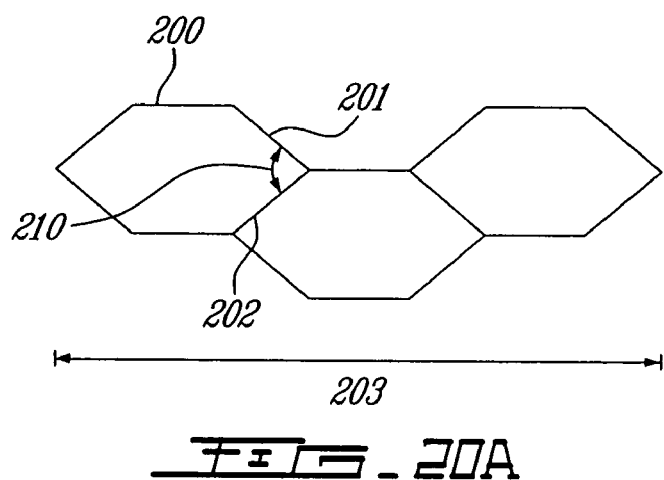
FIGS. 20a-c are magnified illustrations of changing shape of stent cells as the stent is being expanded.
Figure 20B:
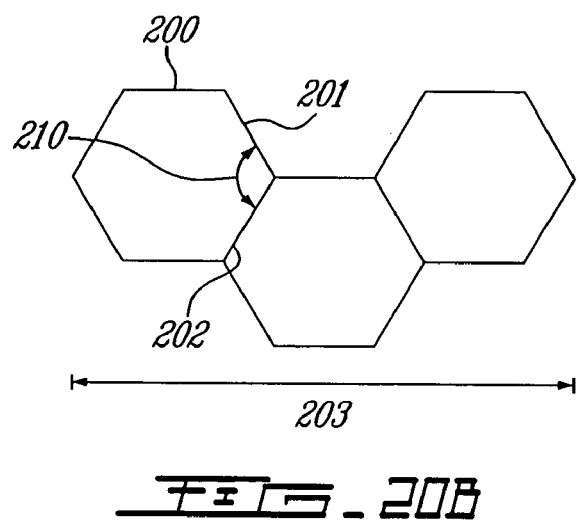
Figure 20C:
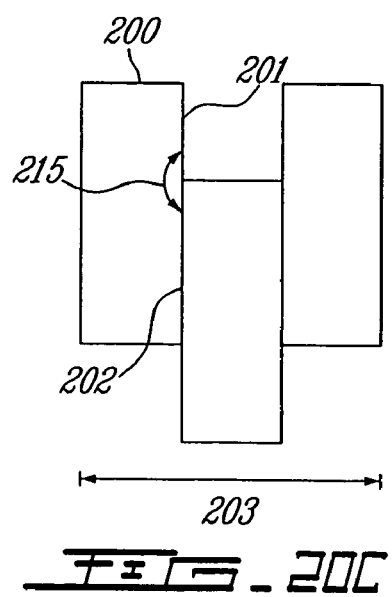

One of the most important issues is the method of attachment of the material 221 to the stent 220. The trans-stent-wall bonds 14 must be long lasting and not cause damage to the material 221 or the stent 220. Methods such as sutures and glue are possible. In addition, the bonds must be designed such that valve integrity is maintained once the valve 223 is expanded from the compressed state. As the stent 221 is expanded, the stent length experiences foreshortening, as each cell in the stent changes shape. FIG. 20*a*-*c* illustrate how a sample length of stent cells 203 experiences foreshortening as the diameter is being expanded. Cell segment 200 maintains a constant length and orientation throughout the expansion. Cell segments 201 and 202 increase the acute angle 210 between them to a maximum angle of 180 degrees 215. Stents that are designed to minimize foreshortening are known in the art, and may also be employed in the prosthetic valve 1.

Figure 15A:
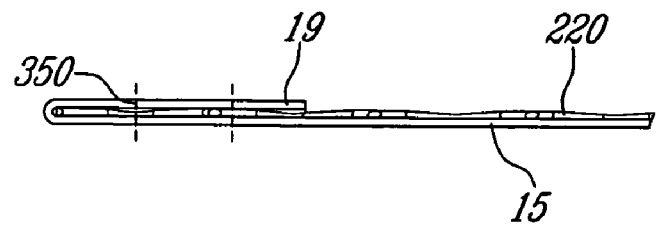
FIGS. 15a-c are magnified cross-sectional views of bonding embodiments for securing the sleeve to the graft through the stent.
Figure 15B:
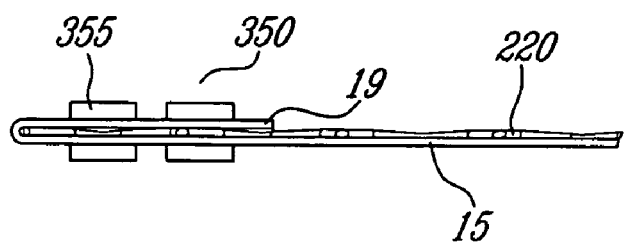
Figure 15C:
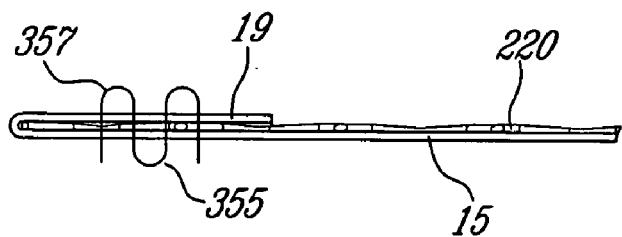

Sutures are a preferred embodiment for material-stent bonds 14. FIGS. 15*a-c* illustrate various suture embodiments used to attach the sleeve 19 to the graft 15 through the stent 220. An important property of the stent that must be considered is the foreshortening of length as the diameter is increased. Therefore sutures should be attached accordingly, preferably to the section of the cell that maintains its original orientation 200. A preferred embodiment of the present invention is to use several isolated, non-continuous sutures 350 to bond the sleeve 19 to the graft 15 through the stent 220. This will provide some room in between the isolated, non-continuous sutures 350, allowing the prosthetic valve 1 to be compressed and re-expanded without damage. This suture technique is illustrated in FIG. 15*a*. FIG. 15*b* is another embodiment of the present invention. Isolated, non-continuous sutures 350 are used in conjunction with pledgets 355. The pledgets 355 are used to protect the underlying material from ripping by providing extra support and distributing the stress of the isolated, non-continuous sutures. This technique is well known and is used by surgeons to protect tissue from sutures. If a continuous suture 357 is used, there is a risk that during expansion of the prosthetic valve 1 some areas may experience high stress, as there is not enough slack available, and rip. However a continuous suture 357 such as illustrated in FIG. 15*c* may be employed as another embodiment of the present invention if the stent 220 selected is designed to experience minimal foreshortening, or if the material 221 and continuous sutures 357 used can withstand the stress.

Another embodiment of the present invention does away completely with sutures. A film bonding technique may be used to connect the metal stent to the Gore-TEX material. If this embodiment is employed, the sleeve 19 then becomes optional, as the graft 15 is already supported and connected to the metal stent 220. However, the sleeve 19 may be desirable in order to prevent tracking of blood between the main pulmonary artery and the stent.

Figure 16:
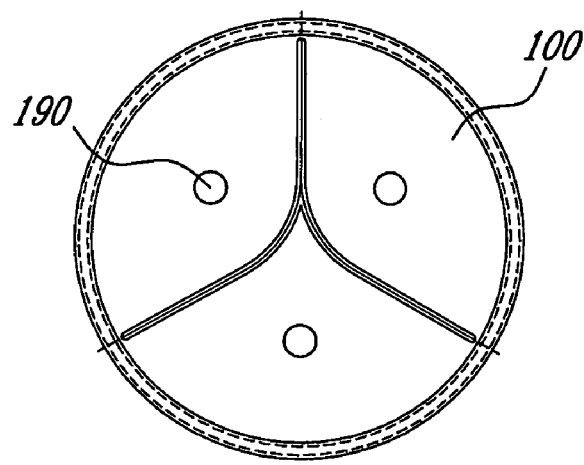
FIG. 16 is a top view illustrating a mechanism for prevention of thrombus formation.

If blood pools and remains stagnant, a thrombus can form, with disastrous consequences. A common solution to this problem is to place patients on anti-coagulants for a period of time as is common practice for some patients with implanted mechanical valves. The prescription of medication can be avoided by making sure that blood is always flowing and never stagnant. However, the present invention avoids this problem without the use of anti-coagulants. A slit, or perforation, is provided in at least one of the leaflets to allow a small amount of regurgitation therethrough even when the leaflets are in contact with each other and the flow of fluid is being impeded. A preferred embodiment of the present invention is illustrated in FIG. 16. The invention achieves this goal by causing a small amount of regurgitation to always be present, even when the leaflets 100 are tight against each other. Small holes 190 can be placed in the portion of the material 221 forming each of the leaflets 100. When the leaflets are formed by pouches, the minimum required to obtain a reduced risk of thrombus is to have a hole in at least one of the pouches. It is preferable to place one hole 190 for each pouch, but more are possible. These holes 190 will make sure that no blood stays stagnant, that the blood will flow even when the leaflets 100 are in contact, by regurgitation. The small amount of regurgitation will not have an impact on the performance of the valve 223 or the health of the patient. The size of the hole 190 must be large enough such that the regurgitating blood flow does not experience a high sheer stress that will damage blood cells and platelets. Another embodiment of the present invention is to coat the prosthetic valve 1 with an anti-coagulant agent, as is optional with some stents. Still another embodiment is to allow cells to infiltrate and coat the material 221 by making the pores in the material large enough. The coat of cells will prevent clots.

Figure 17A:
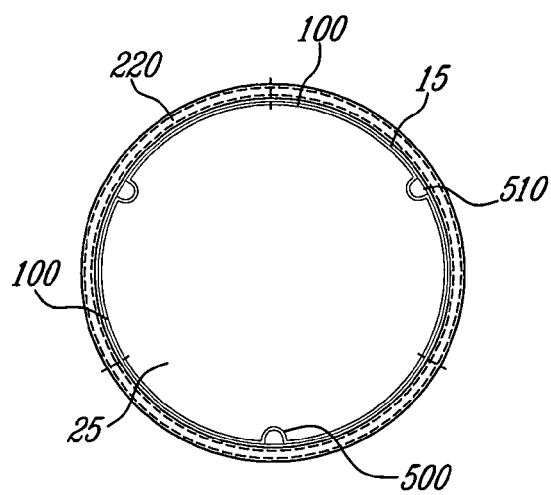
FIGS. 17a-f are top views illustrating mechanisms to overcome the adhesive attraction property of water.
Figure 17B:
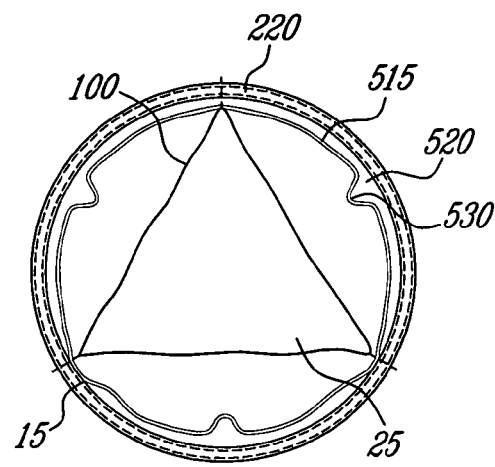
Figure 17C:
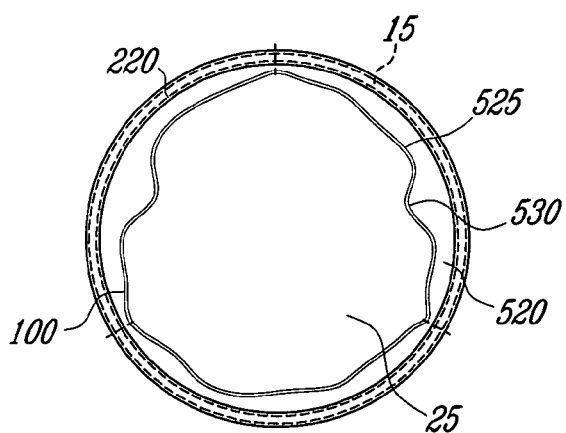
Figure 17D:
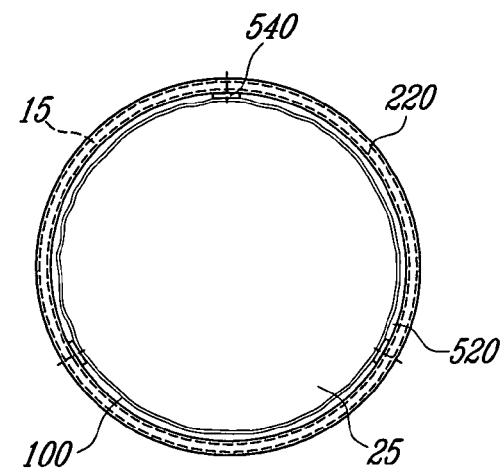

When a smooth plastic-like material is wet, it tends to stick to itself, because of the chemical nature of water. This effect can be experienced after a shower, when a wet plastic shower curtain sticks to itself or to the bathtub. The adhesive attraction property of water may have an effect in the prosthetic valve 1 as it is made out of smooth material 221 that forms the leaflets 100 and graft 15. The leaflets 100 can stick to the graft 15 and refuse to part, thereby creating insufficiency, because the reverse flow of blood 400 will not be impeded. Several solutions are proposed to stop this from happening, and are illustrated in FIGS. 17*a-f*. The preferred embodiment of the present invention is to fold a tiny portion of the middle of each leaflet 100 over itself to form a small pleat 500. This will always ensure that there will be a gap 510 between the leaflet 100 and the graft 15. Leaving a gap 510 will allow blood to enter the non-isolated pouches 180 or the isolated pouches 170, thereby exerting sufficient pressure to displace the leaflets 100 from the graft 15 if they are stuck. A second embodiment of the present invention, as illustrated in FIG. 17*b* is to have a support wire 515, between the graft 15 and the leaflets 100 in order to ensure that a gap 520 is always present, providing access to the non-isolated pouches 180 or to the isolated pouches 170. A third embodiment of the present invention in FIG. 17*c* is to have a support wire 525 attached to the edge of the leaflets 100. These support wires 515 525 can be made of Nitinol, or any other biocompatible flexible wire. The support wires 515 525 can be shaped with a curve 530 to make sure that the leaflet 100 never fully touches the graft 15, always leaving a gap 520. However this embodiment reduces the effective valve orifice area 25. A fourth embodiment of the present invention in FIG. 17*d* is to place raised barriers 540 between the graft 15 and the leaflets 100, at the location of the full material-material bond length 150, or the partial material-material bond length 160. The raised barriers 540 will ensure that a gap 520 is always present between the graft 15 and the leaflets. The prevention mechanism is as described above for the other embodiments.

Figure 17E:
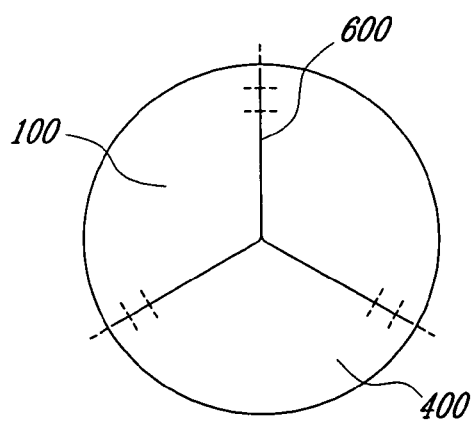
Figure 17F:
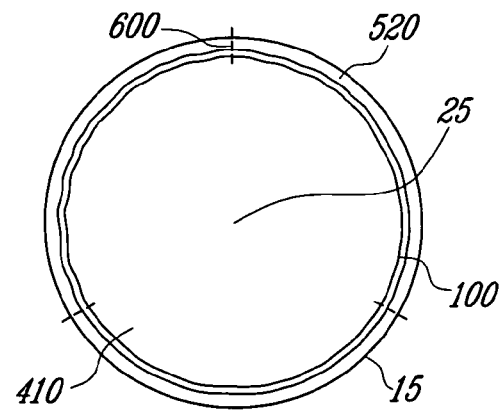

FIG. 17*e* and *f* represent another embodiment of the present invention. A top view of the prosthetic valve 1 is presented, where the leaflets 100 are in contact with one another impeding the reverse flow of blood 400, and where the leaflets open up to an orifice 25 to allow for the forward flow of blood 410. The material-material bond 16 extends to bond and seal the edges of the leaflets 600. The bond and seal of the edges of the leaflets 600 closes the leaflets together in a position that they encounter when blood flow reversed. The bond and seal of the edges of the leaflets 600 extends only for a small percentage of the diameter (e.g. 25%). The result achieved is that a gap 520 is present between the leaflets 100 and the graft 15. Blood will be able to enter the non-isolated cavities 180 or the isolated cavities 170 and force the remainder of the leaflets 100 from the graft 15 to a position that impedes the reverse flow of blood 400. The effective orifice area 25 will be decreased slightly. Therefore the bond sealing the edges of the leaflets 600 must be selected such that cardiac output and normal right ventricle 301 pressure are not adversely affected.

Figure 18A:
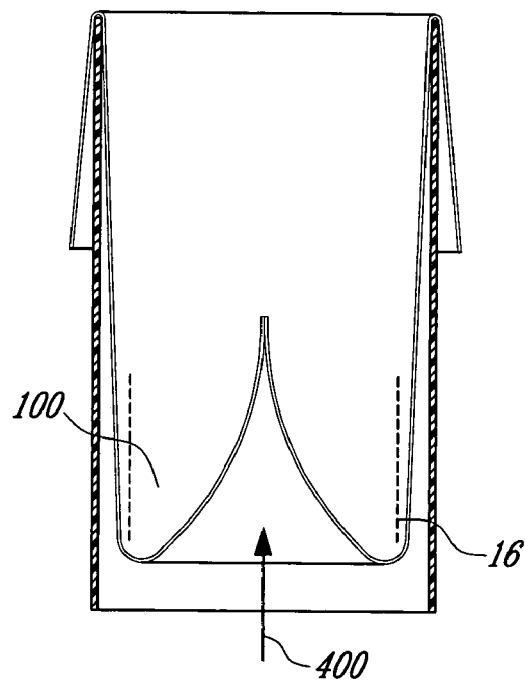
FIGS. 18a-c are side views illustrating mechanisms to assist with closure of the valve during reverse blood flow.
Figure 18B:
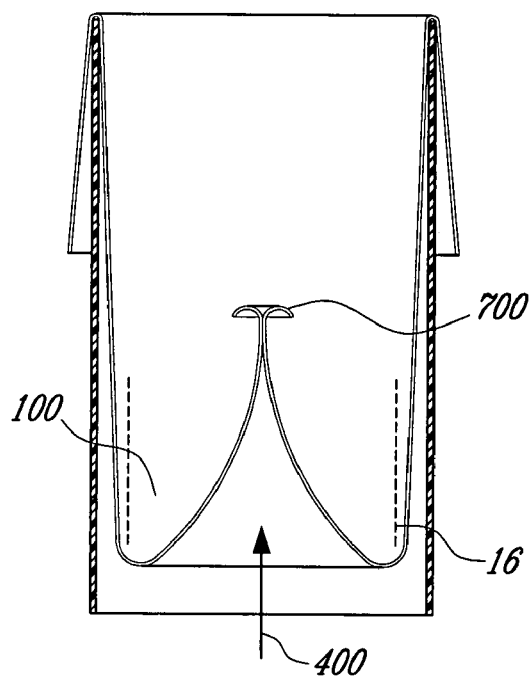
Figure 18C:
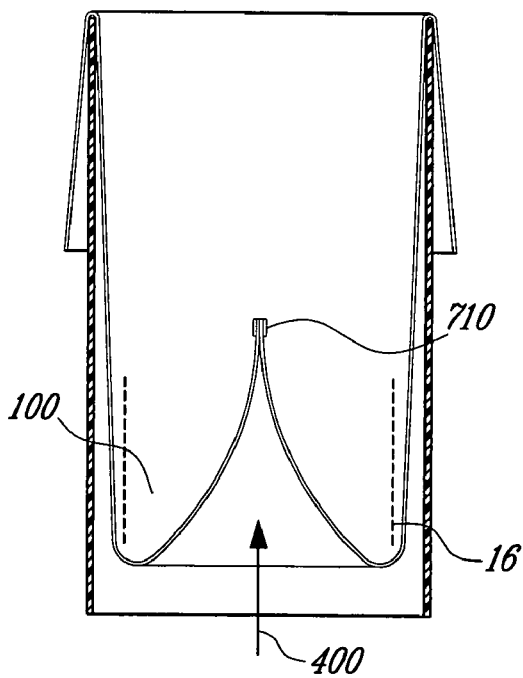

A requirement for proper functionality of the present invention is that the leaflets 100 be in contact with one another upon the reverse flow of blood 400 in order to impede the flow. FIGS. 18a-c disclose several embodiments of the present invention that assist the leaflets 100 in coming into contact, and assisting them in staying in that position throughout that portion of the cardiac cycle. FIG. 18a is a side view illustrating how two of the three leaflets 100 come in contact. The length and shape of the leaflets 100 should reflect the natural pressure profile in the blood vessel. This will help the leaflets 100 close properly as there will not be an excess or lack of material 221. The shear stress at the material-material bond 16 will be minimized. This is a sensitive area that must remain secure for the prosthetic valve to function. An additional embodiment of the present invention is that the edge of the leaflet material can be folded over itself again, creating a lip 700. This lip 700 will better catch the reverse flow of blood 400, and force the three leaflets 100 to come together and close. Still another embodiment of the present invention is that a small nodule 710 can be attached to the edge of the leaflets 100 to make sure that they catch the flow of blood and close in on themselves.

Some patients have very high pressures in their main pulmonary artery 300. In these patients stents may not have enough radial force to prevent migration. FIG. 23 illustrates a preferred embodiment of the present invention used to solve this problem. Small hooks or barbs 750 can be attached to the stent 220 to act as anchors to prevent migration.

The prosthetic valve 1 is based upon the designs of stents that are known in the art, in the sense that an interventional cardiologist or interventional radiologist skilled in deploying stents will be able to quickly work with the invention described. The delivery and deployment method are based on the current state of the art practices employed in the field of interventional medicine, with minimal deviations.

The prosthetic valve 1 can be shipped from the manufacturer in two ways. First, the prosthetic valve 1 can be shipped in an expanded state, separate from the expansion balloon 43. A second method is to ship the prosthetic valve pre-crimped on the expansion balloon 43. The preferred embodiment of the present invention is to ship the prosthetic valve 1 and expansion balloon 43 separately. The interventionist will hand-crimp the prosthetic valve 1 carefully onto the selected expansion balloon 43 to assemble a complete system ready for percutaneous insertion 41. Hand crimping of stents onto expansion balloons 43 is well known in the art and practiced by interventional cardiologists and interventional radiologists. This embodiment allows a physician to select the expansion balloon 43 independently of the stent, to allow better control over sizing. As another advantage of the current invention the prosthetic valve 1 can be stored and shipped in the expanded state.

The interventional cardiologist or interventional radiologist will access the body via the femoral, subclavian or jugular veins for access to the right side of the heart. The prosthetic valve 1 can be delivered through a sheath, over the wire like a stent mounted on a balloon. This is the preferred embodiment for delivery and it is illustrated in FIG. 19. The catheter and sheath housing the stent will be delivered percutaneously through, for example, the femoral vein, up the inferior vena cava 305 to the right atrium 306 of the heart 302, through the tricuspid valve 307, to the right ventricle 301, through the pulmonary valve 308 into the main pulmonary artery 300. The prosthetic valve 1 would be deployed in the main pulmonary artery 300 over the existing pulmonary valve 308, or within the conduit (over its valve, if one is present). If there is no valve, then implantation is in the main pulmonary artery 300 or conduit. If there is a naturally stenotic region, then the prosthetic valve 1 will be placed against this area for security, to prevent migration back into the heart. Once in position, the expansion balloon 43 will be inflated to deliver the prosthetic valve 1. The prosthetic valve 1 will begin to work immediately due to the existing pressure differential between the right ventricle 301 and the main pulmonary artery 300. FIG. 24 illustrates a second embodiment that seeks to solve the problem of a patient's main pulmonary artery 300 or conduit being too big. For example, if the main pulmonary artery 300 is 3 cm in diameter, but the prosthetic valve 1 only expands up to 26 mm, then 2 valves could be delivered instead, one in the left pulmonary artery 331 and one in the right pulmonary artery 330 rather than a single prosthetic valve 1 in the main pulmonary artery 300 (given that the right and left branch pulmonary arteries are generally smaller than the main pulmonary artery). FIG. 26 illustrates this method, in which a first prosthetic valve is provided in a right pulmonary artery adjacent to a main pulmonary artery 806 and a second prosthetic valve is provided in a left pulmonary artery adjacent to the main pulmonary artery 808.

The prosthetic valve 1 size needs to be selected to be slightly larger than the artery diameter in order to ensure a snug fit. It is important that the prosthetic valve 1 be tight against the artery wall to prevent blood from tracking between the graft 15 and the wall of the main pulmonary artery 300. Blood that enters into this space may become trapped, stagnate, and therefore clot.

The prosthetic valve 1 needs to be positioned in the main pulmonary artery 300, without any part of it inside the right ventricle 301, and in such a way that it does not migrate into the heart 302. If part of the prosthetic valve 1 is in the right ventricle 301, the beating heart 302 will cause wear and fatigue to the metal of the stent 220 within a short period of time. The prosthetic valve 301 must also not be positioned too far up in the main pulmonary artery 300. This poses the danger of the graft 15 blocking the entrance to the left branch pulmonary artery 331 or the right branch pulmonary artery 330.

Some very young patients will need the prosthetic valve 1 implanted in them. As the child grows older, the diameter of the main pulmonary artery 300 increases. FIG. 21 illustrates the first prosthetic valve 69 inside the main pulmonary artery 300. A second prosthetic valve 68 will have to be inserted to replace the first prosthetic valve 69 if the pressure gradient between the right ventricle 301 and the main pulmonary artery 300 becomes too large. An expansion balloon 43 will be selected with a diameter equal to or greater than that of the main pulmonary artery 300. The expansion balloon 43 will be guided into position inside the first prosthetic valve 69, and fully expanded to stretch and deform the steel stent 220. The stretched and deformed steel stent 220 will experience foreshortening in length. The sleeve 19, graft 15 and leaflets 100 will also be fully expanded and stretched. This will cause the existing prosthetic valve 1 to cease to function, as the leaflets 100 can no longer touch each other. A second prosthetic valve 68 selected to function at the new diameter is selected. The complete system ready for percutaneous insertion 41 is positioned inside of the first prosthetic valve 69. The second prosthetic valve 68 is expanded. It compresses the leaflets 100 of the first prosthetic valve 69 against the sleeve 19 of the second valve stent 68. A similar method can also be used to replace defective prosthetic valves 1. For example, a prosthetic valve 1 can cease to function due to calcium deposits, fibrous growths or other reasons. As an alternative to this two-step technique for replacement of a defective or outgrown prosthetic valve (consisting of balloon dilatation of the existing prosthetic valve followed by implantation of a second prosthetic valve), the second prosthetic valve may be implanted into the first prosthetic valve without prior balloon dilatation, such that expansion of the second prosthetic valve would result in the simultaneous expansion of the first valve stent along with it.

Another embodiment of the present invention is one in which the stent is made out of a memory metal, and is therefore self-expanding. The delivery method will be different in that case. A balloon delivered over a wire will not be required. The prosthetic valve will be compressed by hand or by other methods and inserted into a sheath. The sheath will be fed through the body lumens and placed into position. The sheath will be retracted exposing the stent. As the sheath is removed, the metal will begin to self-expand. Memory metal allows the retraction of the device into the sheath if it has not been fully deployed, to allow for repositioning. It should be noted that memory metal stents experience more foreshortening during expansion than steel stents, making it more difficult to place them accurately. In addition, memory-metal stents do not have as much radial strength as balloon expandable steel stents.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What is claimed is:

1. A prosthetic valve to be inserted into a body lumen, said valve having leaflets that are spread apart during forward flow of fluid to create an orifice, and said leaflets coming into contact with each other during reverse flow of fluid, thereby impeding said reverse flow of fluid, the valve comprising: a hollow, cylindrical stent having an inner surface and an outer surface, and having a first and a second open end; and a single tubular membrane mounted to said inner surface, said membrane having a graft portion internally folded and bonded to itself at a plurality of points to form pouches including said leaflets, and a sleeve portion on an outer surface of said stent to secure said membrane thereto: wherein said sleeve does not extend beyond an upper half of said stent, and said leaflets are positioned about a lower half of said stent.

2. A prosthetic valve as claimed in claim 1, wherein said sleeve portion is bonded to said graft through said stent by sutures.

3. A prosthetic valve as claimed in claim 1, wherein said pouches are interconnected such that fluid entering a first of said pouches can flow into an adjacent pouch during said reverse flow of fluid to fill said adjacent pouch and cause all of said leaflets to come into contact for said impeding of said reverse flow.

4. A prosthetic valve as claimed in claim 1, wherein said graft portion is bonded to itself at three points to form three pouches, and thereby having three leaflets.

5. A prosthetic valve as claimed in claim 4, wherein said three points are equidistantly spaced about a circumference of said membrane.

6. A prosthetic valve as claimed in claim 1, wherein said membrane is made from a bio-compatible synthetic material.

7. prosthetic valve as claimed in claim 6, wherein said synthetic material has a pore size small enough to prevent cell ingrowth.

8. A prosthetic valve as claimed in claim 1, wherein said stent is balloon-expandable.

9. A prosthetic valve as claimed in claim 1, wherein a base of each of said pouches is shaped to reduce fluid stagnation in said pouches.

10. A prosthetic valve as claimed in claim 1, wherein said pouches comprise at least one hole at a base thereof to cause a minimal amount of fluid to flow therethrough when said leaflets come into contact with each other during reverse flow of fluid.

11. A prosthetic valve as claimed in claim 1, wherein raised barriers are present between said leaflets and said graft to maintain a constant gap therebetween.

12. A prosthetic valve to be inserted into a body lumen, said valve having leaflets that are spread apart during forward flow of fluid to create an orifice, and said leaflets coming into contact with each other during reverse flow of fluid, thereby impeding said reverse flow of fluid, the valve comprising: a hollow, cylindrical stent having en inner surface and an outer surface, and having a first and a second open end; and a tubular membrane mounted to said inner surface, said tubular membrane having a graft portion within said stent internally folded and bonded to itself at a plurality of points to form pouches including said leaflets, and wherein said pouches are interconnected such that fluid entering a first of said pouches can flow into an adjacent pouch during said reverse flow of fluid to fill said adjacent pouch and cause all of said leaflets to come into contact for said impeding of said reverse flow.

13. A prosthetic valve as claimed in claim 12, wherein said tubular membrane has a sleeve portion on an outer surface of said stent to secure said membrane thereto.

14. A prosthetic valve as claimed in claim 12, wherein said pouches comprise at least one hole at a base thereof to cause a minimal amount of fluid to flow therethrough when said leaflets come into contact with each other during reverse flow of fluid.

* * * * *